(12) United States Patent
Soares Da Silva et al.

(10) Patent No.: US 11,034,695 B2
(45) Date of Patent: Jun. 15, 2021

(54) DOPAMINE-β-HYDROXYLASE INHIBITORS

(71) Applicant: BIAL—PORTELA & Cª, S.A., S. Mamede do Coronado (PT)

(72) Inventors: Patrício Soares Da Silva, S. Mamede do Coronado (PT); Tino Rossi, S. Mamede do Coronado (PT); Laszlo Erno Kiss, S. Mamede do Coronado (PT); Alexander Beliaev, S. Mamede do Coronado (PT); Pedro Nuno Leal Palma, S. Mamede do Coronado (PT)

(73) Assignee: BIAL—PORTELA & CA, S.A., Säo Mamede Do Coronado (PT)

( * ) Notice: Subject to any disclaimer, the term of this patent is extended or adjusted under 35 U.S.C. 154(b) by 0 days.

(21) Appl. No.: 16/335,529

(22) PCT Filed: Sep. 22, 2017

(86) PCT No.: PCT/PT2017/050023
§ 371 (c)(1),
(2) Date: Mar. 21, 2019

(87) PCT Pub. No.: WO2018/056855
PCT Pub. Date: Mar. 29, 2018

(65) Prior Publication Data
US 2020/0181148 A1 Jun. 11, 2020

(30) Foreign Application Priority Data

Sep. 23, 2016 (GB) ........................................ 1616201
Aug. 29, 2017 (GB) ........................................ 1713779

(51) Int. Cl.
*C07D 487/04* (2006.01)
*C07D 207/06* (2006.01)
*C07D 207/08* (2006.01)
*C07D 207/27* (2006.01)
*C07D 405/04* (2006.01)
*C07D 409/04* (2006.01)
*A61P 25/34* (2006.01)
*A61P 25/36* (2006.01)
*A61P 25/32* (2006.01)
*A61P 9/12* (2006.01)
*A61P 9/04* (2006.01)

(52) U.S. Cl.
CPC .............. *C07D 487/04* (2013.01); *A61P 9/04* (2018.01); *A61P 9/12* (2018.01); *A61P 25/32* (2018.01); *A61P 25/34* (2018.01); *A61P 25/36* (2018.01); *C07D 207/06* (2013.01); *C07D 207/08* (2013.01); *C07D 207/27* (2013.01); *C07D 405/04* (2013.01); *C07D 409/04* (2013.01)

(58) Field of Classification Search
CPC .................................................. C07D 487/04
See application file for complete search history.

(56) References Cited

U.S. PATENT DOCUMENTS 3,647,790 A 3/1972 Potoski et al.
2019/0337950 A1* 11/2019 Soares Da Silva ....... A61P 9/04

FOREIGN PATENT DOCUMENTS

| WO | 1995/29165 A2 | 11/1995 | |
|---|---|---|---|
| WO | 2002/092019 A2 | 11/2002 | |
| WO | 2004/033447 A1 | 4/2004 | |
| WO | 2008/085008 A1 | 7/2008 | |
| WO | 2008/136695 A1 | 11/2008 | |
| WO | 2009/015248 A1 | 1/2009 | |
| WO | 2014/127350 A1 | 8/2014 | |
| WO | 2018/056854 A1 | 3/2018 | |
| WO | 2018/056855 A1 | 3/2018 | |
| WO | WO-2018056854 A1 * | 3/2018 | ........... C07D 207/08 |

OTHER PUBLICATIONS

International Search Report and Written Opinion for Application No. PCT/PT2018/050043, dated Feb. 15, 2019, 10 Pages.
U.S. Appl. No. 16/335,521, filed Mar. 21, 2019, 2019-0337950, Published.
U.S. Appl. No. 16/769,045, filed Jun. 2, 2020, Pending.
International Search Report for Application No. PCT/PT2017/050022, dated Nov. 24, 2017, 4 pages.
International Search Report for Application No. PCT/PT2017/050023, dated Dec. 15, 2017, 3 pages.
Beliaev et al., Dopamine beta-Monooxygenase: Mechanism, Substrates and Inhibitors. Current Enzyme Inhibition. 2009;5:27-43.

(Continued)

*Primary Examiner* — John S Kenyon
(74) *Attorney, Agent, or Firm* — McCarter & English, LLP; Steven G. Davis; Wei Song

(57) ABSTRACT

This invention relates to: (a) compounds of Formula Ia (with R1, R4, R5, R6, n and A as defined herein) and pharmaceutically acceptable salts or solvates thereof that are useful as dopamine-β-hydroxylase inhibitors; (b) pharmaceutical compositions comprising such compounds, salts or solvates; (c) the use of such compounds, salts or solvates in therapy; (d) therapeutic methods of treatment using such compounds, salts or solvates; and (e) processes and intermediates useful for the synthesis of such compounds.

25 Claims, No Drawings

(56) References Cited

OTHER PUBLICATIONS

Goldstein et al., Inhibition of Dopamine-beta-Hydroxylase by Disulfiram. Life Sciences. 1964;3:763-767.

Hidaka, Fusaric (5-butylpicolinic) acid, an inhibitor of dopamine beta-hydroxylase, affects serotonin and noradrenaline. Nature. May 7, 1971;231(5297):54-5.

Johnson et al., In vivo inhibition of dopamine beta-hydroxylase by 1-phenyl-3-(2-thiazolyl)-2-thiourea (U-14,624). J Pharmacol Exp Ther. Jan. 1970;171(1):80-7.

Koczka et al., Adatok AZ 1,2,4-Triazol-Szarmazekok Antimikrobas Hatasahoz. (Antimicrobial Activity of 1,2,4-Triazole Derivatives.) Sejtosztodas Farmakologiaja. 1979;8(1):79-100.

Lippmann et al., Dopamine-hydroxylase inhibition by dimethyldithiocarbamate and related compounds. Biochem Pharmacol. Oct. 1969;18(10):2507-16.

Stanley et al., Catecholamine modulatory effects of nepicastat (RS-25560-197), a novel, potent and selective inhibitor of dopamine-beta-hydroxylase. Br J Pharmacol. Aug. 1997;121(8):1803-9.

\* cited by examiner

DOPAMINE-β-HYDROXYLASE INHIBITORS

CROSS-REFERENCE TO RELATED APPLICATIONS

This application is a U.S. national stage filing, under 35 U.S.C. § 371(c), of International Application No. PCT/PT2017/050023, filed on Sep. 22, 2017, which claims priority to United Kingdom Patent Application No. 1713779.5, filed on Aug. 29, 2017; and United Kingdom Patent Application No. 1616201.8, filed on Sep. 23, 2016. The entire contents of each of the aforementioned applications are incorporated herein by reference.

FIELD OF THE INVENTION

This invention relates to: (a) compounds and pharmaceutically acceptable salts or solvates thereof that are useful as dopamine-β-hydroxylase inhibitors; (b) pharmaceutical compositions comprising such compounds, salts or solvates; (c) the use of such compounds, salts or solvates in therapy; (d) therapeutic methods of treatment using such compounds, salts or solvates; and (e) processes and intermediates useful for the synthesis of such compounds.

BACKGROUND OF THE INVENTION

The enzyme dopamine-β-hydroxylase (DβH), also known as dopamine β-monooxygenase, is expressed both in the periphery and the central nervous system (CNS). DβH catalyses the specific hydroxylation of dopamine (DA) to produce norepinephrine, also known as noradrenaline (NA). As such, inhibitors of DβH can inhibit the biosynthesis of NA, limiting its concentration and increasing DA levels.

Conventionally, interest in the development of inhibitors of DβH had centred on the hypothesis that inhibition of this enzyme may provide significant clinical improvements in patients suffering from cardiovascular disorders such as hypertension or chronic heart failure. The rationale for the use of DβH inhibitors is based on their capacity to inhibit the biosynthesis of NA, which is achieved via enzymatic hydroxylation of DA. Reduction of the biosynthesis of NA via inhibition of DβH can directly dampen sympathetic nerve function, the activation of which is the principal clinical manifestation of congestive heart failure (Parmley, W. W., Clin. Cardiol., 18: 440-445, 1995). Therefore, peripheral DβH inhibitors reduce sympathetic drive. Congestive heart failure patients have elevated concentrations of plasma noradrenaline (Levine, T. B. et al., Am. J. Cardiol., 49:1659-1666, 1982), increased central sympathetic outflow (Leimbach, W. N. et al., Circulation, 73: 913-919, 1986) and augmented cardiorenal noradrenaline spillover (Hasking, G. J. et al., Circulation, 73:615-621, 1966). Prolonged and excessive exposure of the myocardium to noradrenaline may lead to down-regulation of cardiac $\beta_1$-adrenoceptors, remodelling of the left ventricle, arrhythmias and necrosis, all of which can diminish the functional integrity of the heart. Congestive heart failure patients who have high plasma concentrations of noradrenaline also have the most unfavourable long-term prognosis (Cohn, J. N. et al., N. Engl. J. Med., 311:819-823, 1984). Of greater significance is the observation that plasma noradrenaline concentrations are already elevated in asymptomatic patients with no overt heart failure and can predict ensuing mortality and morbidity (Benedict, C. R. et al., Circulation, 94:690-697, 1996). An activated sympathetic drive is not therefore merely a clinical marker of congestive heart failure, but may contribute to progressive worsening of the disease.

DβH inhibitors may also find application in disorders of the CNS, including drug addiction, psychiatric disorders, reduced cognition or dementia. For example, cocaine primarily acts through inhibition of presynaptic dopamine (DA) transporters as well as the serotonin and norepinephrine transporters. Increased levels of synaptic DA and, thereby, DA receptor binding following cocaine administration is a key mechanism through which cocaine is reinforcing. Cocaine also modulates the endogenous opioid system, especially μ-opioid receptors (MOR), κ-opioid receptors (KOR), and preprodynorphin. Whereas stimulation of dopaminergic pathways may be sufficient to cause the reinforcing effects of cocaine, DA transporter gene deletion studies have shown that this pathway is not essential to the development of cocaine self-administration. Selective gene disruption of the MOR will, however, prevent the development of cocaine self-administration.

Disulfiram (Antabuse), which inhibits aldehyde dehydrogenase (ALDH) and has been used for more than 50 years in the treatment of alcoholism (Fuller, R. K. et al., J. Amer. Med. Assoc., 256: 1449-55, 1986), was found to reduce alcohol and cocaine intake in co-dependent patient population (Carroll, K. M. et al., Arch. Gen. Psychiatry, 61: 264-72, 2000; Carroll, K. M. et al., Addiction, 93: 713-27, 1998; Carroll, K. M. et al., J. Stud. Alcohol, 54: 199-208, 1993). Surprisingly, further studies revealed that disulfiram was at least as effective at treating cocaine addicts who do not consume alcohol, and may even be more effective (Carroll, K. M. et al., Arch. Gen. Psychiatry, 61: 264-72, 2004; George, T. P. et al., Biol Psychiatry, 47: 1080-6, 2000; Petrakis, I. L. et al., Addiction, 95: 219-28, 2000). Therefore, an ALDH-independent mechanism must be responsible for the ability of disulfiram to promote cocaine abstinence (Gaval-Cruz, M. et al., Mol. Interv., 9: 175-87, 2009; Weinshenker, D. et al., Neuropsychopharmacology, 32: 1433-51, 2007). Subsequently, Schroeder et al. tested the effects of disulfiram on cocaine and food self-administration behaviour and drug-primed reinstatement of cocaine seeking in rats (Schroeder, J. P. et al., Neuropsychopharmacology, 35: 2440-9, 2010). Their results suggest that disulfiram's efficacy in the treatment of cocaine addiction is associated with the inhibition of DβH and interference with the ability of environmental stimuli to trigger relapse (Schroeder, J. P. et al., Neuropsychopharmacology, 35: 2440-9, 2010).

Furthermore, the noradrenergic system plays a role in a number of cognitive domains, including working memory, attention, and memory consolidation (Coull, J. T. et al., NeuroImage, 10: 705-15, 1999; McGaugh, J. L. et al., Psychopharmacology, 202: 3-14, 2009; Sara, S. J., Neuroscience, 10: 211-23, 2009). However, noradrenergic system activity in excess may impair cognition. Animal studies have shown associations between excess noradrenergic activity and impairments in attention and working memory (Arnsten, A. F., Nat. Rev. Neurosci., 10: 410-22, 2009; Sara, S. J., Neuroscience, 10: 211-23, 2009). Other studies show decreased cognitive performance in people placed under stress conditions, suggesting excess noradrenergic activity affects human cognition as well (Campbell, H. L. et al., Pharmacol. Biochem. Behav., 88: 222-9, 2008; Hermans, E. J. et al., Science, 334: 1151-3, 2011). Given this association between cognitive performance and noradrenergic system activity, there remains the question of whether differences in basal levels of activity may relate to differences in cognitive performance and whether this relationship is also influenced by age. Noradrenergic system activity appears higher in older compared with younger adults, both peripherally and in the CNS (Featherstone, J. A. et al., J. Gerontol., 42, 271-6, 1987; Lawlor, B. A. et al., Biol. Psychiatry, 38: 185-8, 1995; Supiano, M. A. et al., Am. J. Physiol., 259: E422-31, 1990). Previously it has been demonstrated that the concentration of cerebrospinal fluid NA was higher in older compared with younger adults, but it is not known whether noradrenergic system age differences may be a factor in cognitive differences. Numerous studies have linked excess noradrenergic activity with cognitive impairment. As such, DβH inhibitors may find application in enhancing cognition, especially in those suffering from dementia, including frontotemporal dementia (FTD), Parkinson disease and Alzheimer disease (AD), or Mild Cognitive Impairment (MCI).

Several inhibitors of DβH have been thus far reported in the literature. Early first and second generation examples such as disulfiram (Goldstein, M. et al., Life Sci., 3:763, 1964) and diethyldithiocarbamate (Lippmann, W. et al., Biochem. Pharmacol., 18: 2507, 1969) or fusaric acid (Hidaka, H. Nature, 231, 1971) and aromatic or alkyl thioureas (Johnson, G. A. et al, J. Pharmacol. Exp. Ther., 171: 80, 1970) were found to be of low potency, exhibited poor selectivity for DβH and caused toxic side effects. The third generation of DβH inhibitors, however, were found to have much greater potency, such as, for example, nepicastat (RS-25560-197, $IC_{50}$ 9 nM) (Stanley, W. C., et al., Br. J. Pharmacol., 121: 1803-1809, 1997), which was developed to early clinical trials. Although it was initially developed for peripheral indications (hypertension and congestive heart failure), an important discovery was that nepicastat was found to cross the blood-brain barrier (BBB), and was thereby able to cause central as well as peripheral effects.

Nepicastat and its analogues are disclosed in WO95/29165. Furthermore, WO 2004/033447 and WO 2008/136695 disclose DβH inhibitors having high potency and significantly reduced brain access, giving rise to potent and peripherally selective DβH inhibitors. However, these compounds would either not exhibit an effect in the CNS or would act primarily in the periphery, potentially resulting in unwanted secondary effects in the cardiovascular system or systemic tissues such as reduced sympathetic drive. A review of the mechanism, substrates and inhibitors of DβH, is given by Beliaev, A., et al. in Current Enzyme Inhibition, 5, 27-43, 2009.

Therefore, there remains an unfulfilled clinical requirement for a potent, non-toxic and peripherally selective inhibitor of DβH, which could be used for treatment of certain cardiovascular disorders such as Hypertension, Chronic Heart Failure and Pulmonary Arterial Hypertension (PAH). A DβH inhibitor with similar or even greater potency than nepicastat, but devoid of CNS effects (i.e. unable to efficiently cross the BBB), yet exhibiting a long residence time in the periphery so as to provide a long duration of DβH inhibition would provide a significant improvement over all DβH inhibitor compounds thus far described in the prior art. Additionally, such compounds would preferably be orally bioavailable, highly soluble and easier and cheaper to synthesise.

There also remains an unfulfilled clinical requirement for a potent, non-toxic and CNS-penetrant/active inhibitor of DβH with suitable pharmacokinetic properties, which could be used for treatment of certain CNS disorders, including cocaine addiction, alcohol addiction, adjunct opioid addiction, cognition decline in FTD, cognition decline in MCI, cognition decline in AD, attention deficit-hyperactive disorder (ADHD), post-traumatic stress disorder (PTSD) and unipolar depression. A DβH inhibitor with similar or even greater potency than nepicastat and with beneficial CNS effects—including the ability to cross the BBB and exhibit a long residence time in the brain so as to provide a long duration of DβH inhibition in the CNS—would provide a significant improvement over all DβH inhibitor compounds thus far described in the prior art. Additionally, such compounds would preferably be orally bioavailable and easier and cheaper to synthesise.

SUMMARY OF THE INVENTION

The present invention provides a compound of formula Ia, or a pharmaceutically acceptable salt or solvate thereof:

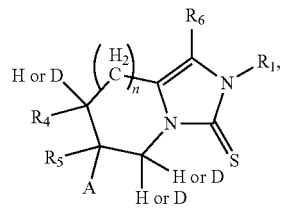

(Ia)

wherein:
$R_1$ is hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl or amino;
$R_4$ is hydrogen or $C_1$-$C_3$ alkyl;
$R_5$ is hydrogen or $C_1$-$C_2$ alkyl;
or $R_4$ and $R_5$ combine, together with the carbon atom to which they are attached, to form a cyclopropyl ring wherein the $CH_2$ moiety is optionally substituted with two deuterium (D) atoms;
$R_6$ is $C_1$-$C_6$ alkyl or partially or fully deuterated $C_1$-$C_6$ alkyl;
A is $C_5$-$C_7$ cycloalkyl, furanyl, thiophenyl, methylthiophenyl or

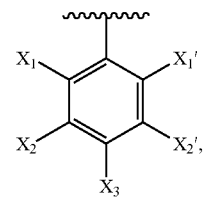

wherein:
$X_1$ is hydrogen, halo or methyl;
$X_1'$ is hydrogen or halo;
$X_2$ is hydrogen, halo or methyl;
$X_2'$ is hydrogen or halo;
$X_3$ is hydrogen or fluoro;
n is 0 or 1, and when n is 0 a single bond joins the carbon atoms to which the $CH_2$ moeity would be attached when n is 1.

This invention is also directed to compounds of formula Ia, as defined above, or a pharmaceutically acceptable salt or solvate thereof, for use in therapy.

This invention is also directed to compounds of formula Ia, as defined above, or a pharmaceutically acceptable salt or solvate thereof, for use in the treatment of conditions ameliorated by inhibition of DβH within the CNS.

This invention is also directed to compounds of formula Ia, as defined above, or a pharmaceutically acceptable salt or solvate thereof, in the manufacture of a medicament for treatment of conditions ameliorated by inhibition of DβH within the CNS.

This invention is also directed to a method for treating or preventing conditions ameliorated by inhibition of DβH within the CNS comprising administering a therapeutically effective amount of a compound of formula Ia, as defined above, or a pharmaceutically acceptable salt or solvate thereof, to a patient in need thereof.

This invention is also directed to a pharmaceutical composition comprising (i) a therapeutically effective amount of a compound of formula Ia, as defined above, or a pharmaceutically acceptable salt or solvate thereof; and (ii) a pharmaceutically acceptable excipient.

DETAILED DESCRIPTION OF THE EMBODIMENTS

A. Definitions

"$C_1$-$C_6$ alkyl" means a monovalent unsubstituted saturated straight-chain or branched-chain hydrocarbon radical having from 1 to 6 carbon atoms. "$C_1$-$C_2$ alkyl", "$C_1$-$C_3$ alkyl", "$C_1$-$C_4$ alkyl" and "$C_1$-$C_5$ alkyl" have analogous meanings.

"partially or fully deuterated $C_1$-$C_6$ alkyl" means a $C_1$-$C_6$ alkyl wherein some or all of the hydrogen atoms, respectively, have been selectively replaced by deuterium.

"$C_3$-$C_6$ cycloalkyl" means a monovalent unsubstituted saturated cyclic hydrocarbon radical having from 3 to 6 carbon atoms. "$C_5$-$C_7$ cycloalkyl" has analogous meaning.

"$C_2$-$C_6$ cyanoalkyl" means a monovalent cyano-substituted saturated straight-chain or branched-chain hydrocarbon radical having from 2 to 6 carbon atoms including that which forms the cyano group.

"$C_1$-$C_6$ mercaptoalkyl" means a monovalent thiol-substituted saturated straight-chain or branched-chain hydrocarbon radical having from 1 to 6 carbon atoms.

"halo" means a fluorine (which may be depicted as —F), chlorine (which may be depicted as —Cl), bromine (which may be depicted as —Br) or iodine (which may be depicted as —I) radical.

"amino" means —$NH_2$.

"Pharmaceutically acceptable salt" means a salt such as those described in standard texts on salt formation, see for example: P. Stahl, et al., Handbook of Pharmaceutical Salts: Properties, Selection and Use (VCHA/Wiley-VCH, 2002), or S. M. Berge, et al., "Pharmaceutical Salts" (1977) *Journal of Pharmaceutical Sciences*, 66, 1-19.

"Pharmaceutically acceptable solvate" means a molecular complex comprising the compound of the invention and one or more pharmaceutically acceptable solvent molecules, for example, water or ethanol. The term "hydrate" may be employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

"Pharmaceutically acceptable excipient" means any ingredient of a pharmaceutical composition other than the compound(s) of the invention, or other known pharmacologically active components. The choice of excipient will to a large extent depend on factors such as the particular mode of administration, the effect of the excipient on solubility and stability, and the nature of the dosage form.

"Therapy", "treatment" and "treating" include both preventative and curative treatment of a condition, disease or disorder. It also includes slowing, interrupting, controlling or stopping the progression of a condition, disease or disorder. It also includes preventing, curing, slowing, interrupting, controlling or stopping the symptoms of a condition, disease or disorder.

Other variations to the disclosed embodiments can be understood and effected by those skilled in the art in practicing the claimed invention, from a study of the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

B. Compounds

The invention provides a compound of formula Ia, as defined above, or a pharmaceutically acceptable salt or solvate thereof:

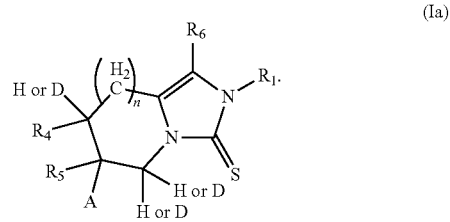

(Ia)

B0. Core Structures

In some embodiments of formula Ia, n is 0 and a single bond joins the carbon atoms to which the $CH_2$ moiety would be attached when n is 1 to form a structure of formula Ib

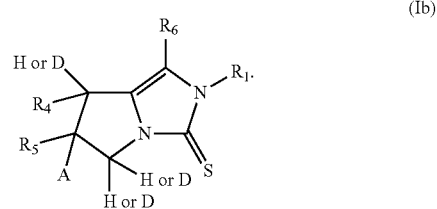

(Ib)

In some embodiments of formula Ia, $R_4$ and $R_5$ combine, together with the carbon atom to which they are attached, to form a structure of formula Ic having a cyclopropyl ring wherein the $CH_2$ moiety is optionally substituted with two deuterium atoms:

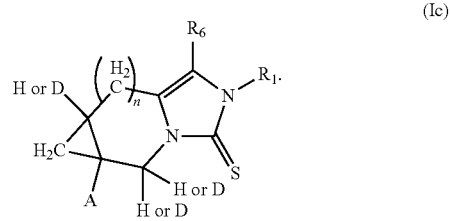

(Ic)

In some embodiments more than 50%, preferably more than 90%, more preferably more than 95% and even more preferably more than 99% of substituents $R_5$ and A of compounds of formula Ia have the stereochemical configuration of formula Id

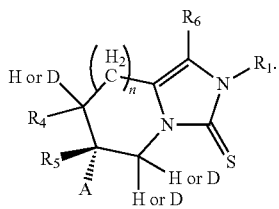

(Id)

In some embodiments more than 50%, preferably more than 90%, more preferably more than 95% and even more preferably more than 99% of substituents $R_5$ and A of compounds of formula Ia have the stereochemical configuration of formula Ie

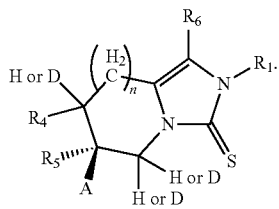

(Ie)

Preferred embodiments of formula Ia include compounds of formula Ih.

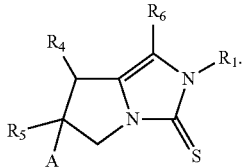

(Ih)

In some particularly preferred embodiments of formula Ih more than 50%, preferably more than 90%, more preferably more than 95% and even more preferably more than 99% of substituents $R_5$ and A of compounds of formula Ih have the stereochemical configuration of formula Iu

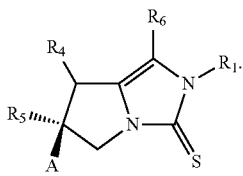

(Iu)

In other particularly preferred embodiments of formula Ih more than 50%, preferably more than 90%, more preferably more than 95% and even more preferably more than 99% of substituents $R_5$ of compounds of formula Ih have the stereochemical configuration of formula Iv

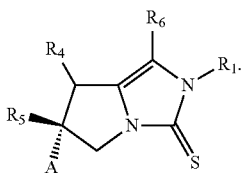

(Iv)

Other preferred embodiments of formula Ia include compounds of formula Ik.

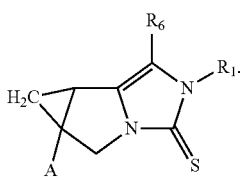

(Ik)

In some particularly preferred embodiments of formula Ik more than 50%, preferably more than 90%, more preferably more than 95% and even more preferably more than 99% have the stereochemical configuration of formula In.

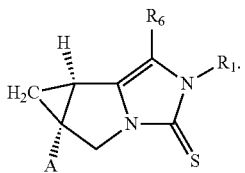

(In)

B1. Substituent $R_1$ $R_1$ is selected from the group consisting of hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl and amino.

$R_1$ is preferably selected from the group consisting of hydrogen and $C_1$-$C_6$ alkyl.

In some embodiments $R_1$ is hydrogen.
In some embodiments $R_1$ is $C_1$-$C_6$ alkyl.
In some embodiments $R_1$ is partially deuterated $C_1$-$C_6$ alkyl.
In some embodiments $R_1$ is fully deuterated $C_1$-$C_6$ alkyl.
In some embodiments $R_1$ is $C_3$-$C_6$ cycloalkyl.
In some embodiments $R_1$ is $C_2$-$C_6$ cyanoalkyl.
In some embodiments $R_1$ is $C_1$-$C_6$ mercaptoalkyl.
In some embodiments $R_1$ is amino.

$R_1$ is preferably selected from the group consisting of hydrogen, methyl, d3-methyl, propyl, cyclopropyl, cyanomethyl, mercaptoethyl and amino.

$R_1$ is more preferably selected from the group consisting of hydrogen and methyl.

In some embodiments $R_1$ is preferably hydrogen.
In some embodiments $R_1$ is preferably methyl.
In some embodiments $R_1$ is preferably d3-methyl.
In some embodiments $R_1$ is preferably propyl.
In some embodiments $R_1$ is preferably cyclopropyl.
In some embodiments $R_1$ is preferably cyanomethyl.
In some embodiments $R_1$ is preferably mercaptoethyl.
In some embodiments $R_1$ is preferably amino.

$R_1$ is most preferably hydrogen.

B2. Substituent $R_4$ (When Not Combined with $R_5$)

$R_4$ is selected from the group consisting of hydrogen and $C_1$-$C_3$ alkyl.

In some embodiments $R_4$ is hydrogen.

In some embodiments $R_4$ is $C_1$-$C_3$ alkyl.

$R_4$ is preferably selected from the group consisting of hydrogen and methyl.

In some embodiments $R_4$ is preferably hydrogen.

In some embodiments $R_4$ is preferably methyl.

$R_4$ is most preferably hydrogen.

B3. Substituent $R_5$ (When Not Combined with $R_4$)

$R_5$ is selected from the group consisting of hydrogen and $C_1$-$C_2$ alkyl.

In some embodiments $R_5$ is hydrogen.

In some embodiments $R_5$ is $C_1$-$C_2$ alkyl.

$R_5$ is preferably selected from the group consisting of hydrogen and methyl.

In some embodiments $R_5$ is preferably hydrogen.

In some embodiments $R_5$ is preferably methyl.

$R_5$ is most preferably hydrogen.

B4. Substituent $R_6$ $R_6$ is selected from the group consisting of $C_1$-$C_6$ alkyl, and partially or fully deuterated $C_1$-$C_6$ alkyl.

$R_6$ is preferably $C_1$-$C_6$ alkyl.

In some embodiments $R_6$ is partially deuterated $C_1$-$C_6$ alkyl.

In some embodiments $R_6$ is fully deuterated $C_1$-$C_6$ alkyl.

$R_6$ is preferably selected from the group consisting of methyl, n-butyl and $d_3$-methyl.

In some embodiments $R_6$ is preferably methyl.

In some embodiments $R_6$ is preferably n-butyl.

In some embodiments $R_6$ is preferably d3-methyl.

$R_6$ is most preferably methyl.

B5. Substituent A

A is selected from the group consisting of $C_5$-$C_7$ cycloalkyl, furanyl, thiophenyl, methylthiophenyl and

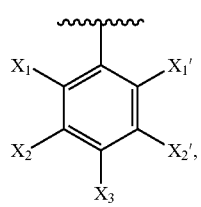

wherein:

$X_1$ is hydrogen, halo or methyl;

$X_1'$ is hydrogen or halo;

$X_2$ is hydrogen, halo or methyl;

$X_2'$ is hydrogen or halo; and $X_3$ is hydrogen or fluoro.

Preferably A is

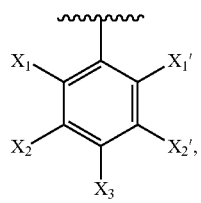

wherein $X_1$, $X_1'$, $X_2$, $X_2'$ and $X_3$ are as defined above.

More preferably A is

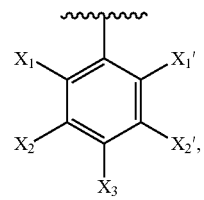

wherein:

$X_1$ is hydrogen, fluoro, chloro or methyl;

$X_1'$ is hydrogen, fluoro or chloro;

$X_2$ is hydrogen, fluoro, chloro, bromo or methyl;

$X_2'$ is hydrogen, fluoro, chloro or bromo; and $X_3$ is hydrogen or fluoro.

In one preferred embodiment not all of $X_1$, $X_1'$, $X_2$, $X_2'$ and $X_3$ are hydrogen. Preferably A is selected from the group consisting of

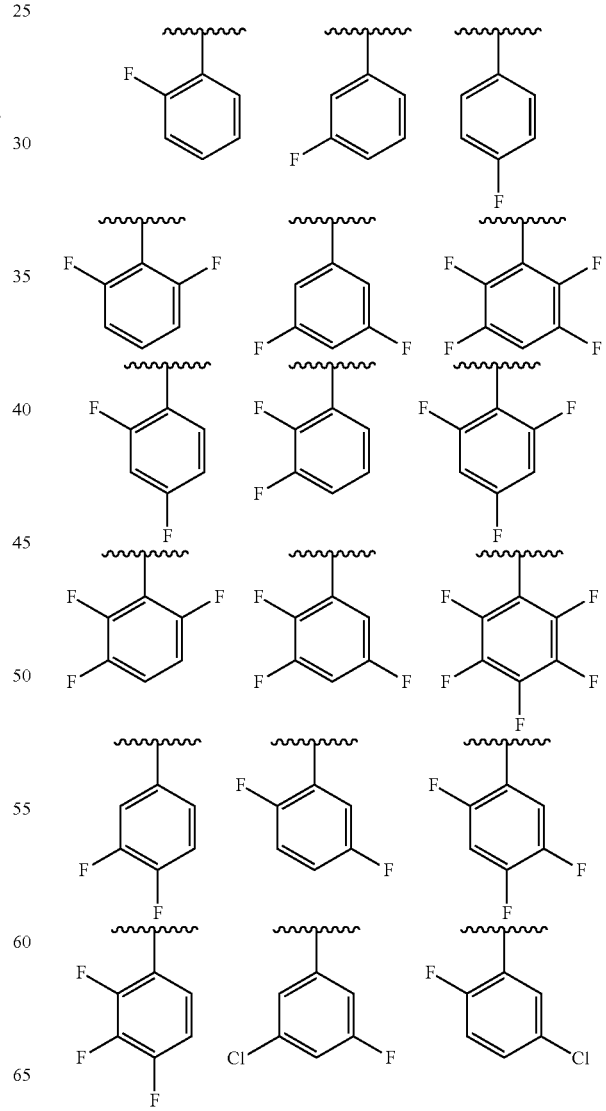

-continued

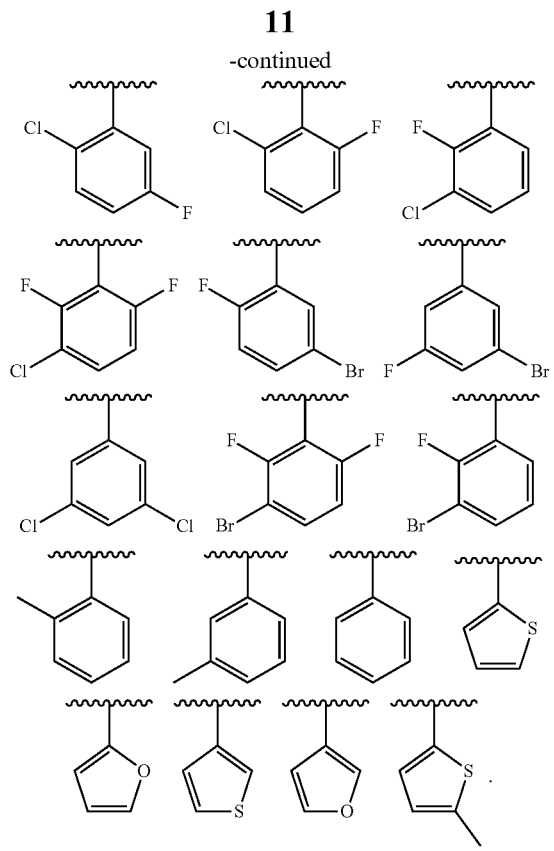

Most preferably A is selected from the group consisting of

-continued

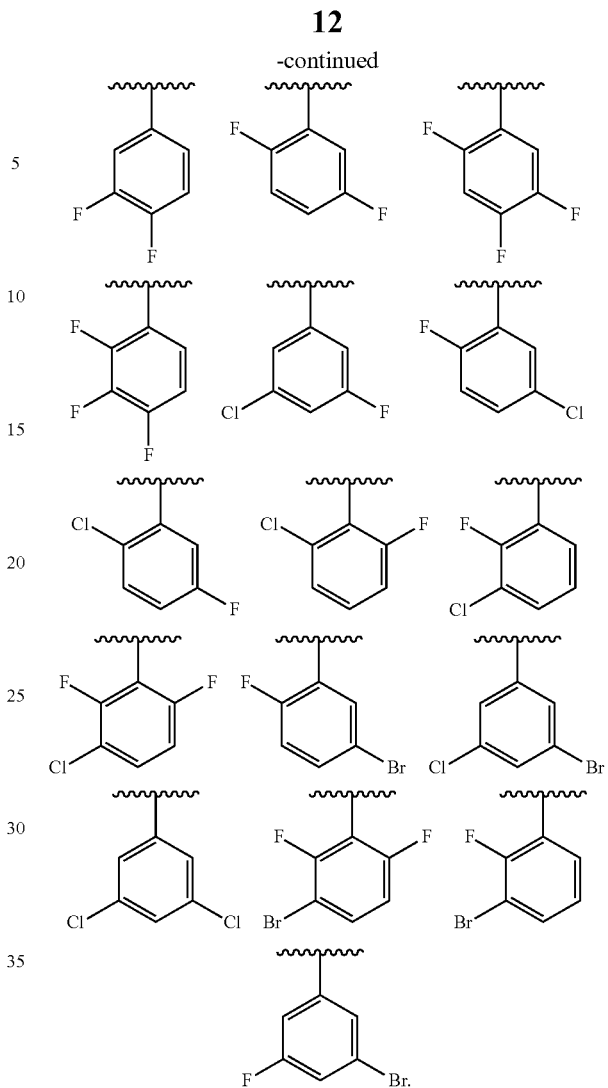

B6. Specific Embodiments of Compounds of Formula I

Various embodiments of substituents $R_1$, $R_4$, $R_5$, $R_6$, A, X, $X_1$, $X_1'$, $X_2$, $X_2'$ and $X_3$ have been discussed in B1 to B5 above. These "substituent" embodiments can be combined with any of the "core structure" embodiments, discussed in B0 above, to form further embodiments of compounds of formula Ia. All embodiments of compounds of formula Ia formed by combining the "substituent" embodiments and "core structure" embodiments, discussed above, are within the scope of Applicants' invention, and some preferred further embodiments of the compounds of formula I are provided below.

In some embodiments of formula Ia, structures of formula Ih, Ik, and In (in particular formula Ih) are highly preferred

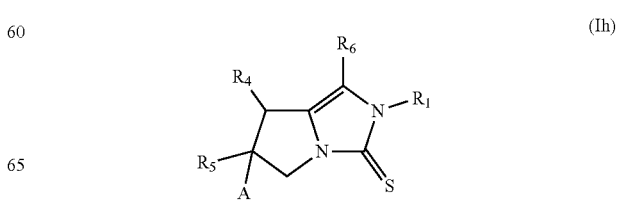

(Ih)

-continued

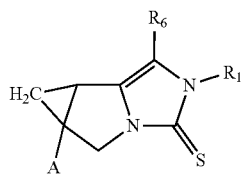
(Ik)

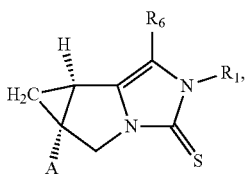
(In)

wherein:

R₁ is selected from the group consisting of hydrogen and methyl;

R₄ (if present) is selected from the group consisting of hydrogen and methyl;

R₅ (if present) is selected from the group consisting of hydrogen and methyl;

R₆ is methyl; and

A is selected from the group consisting of

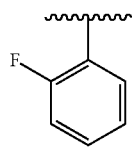 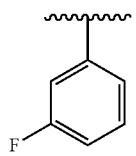 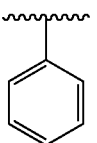

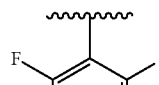 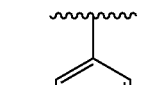 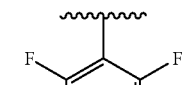

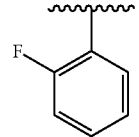 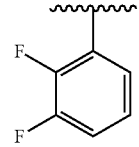 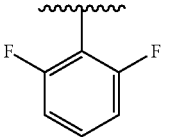

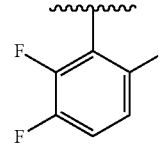 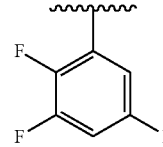 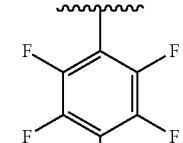

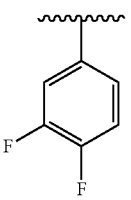 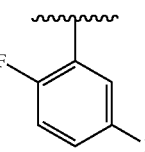 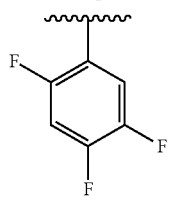

-continued

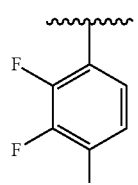 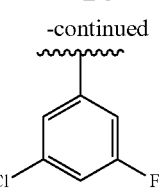 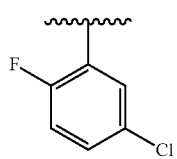

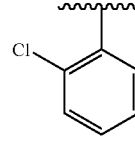 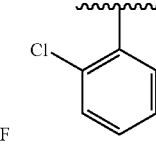 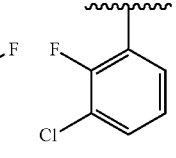

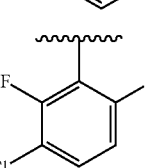 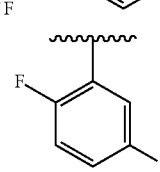 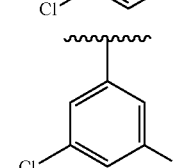

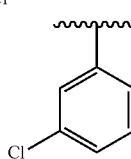 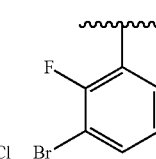 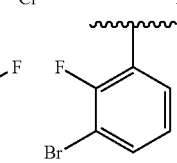

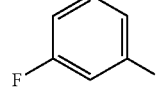

In some embodiments of formula Ia, structures of formula Ir are even more highly preferred

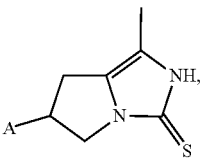
(Ir)

wherein:

A is selected from the group consisting of

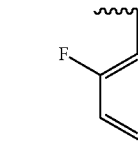 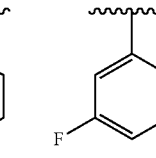 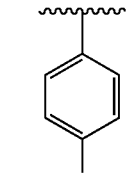

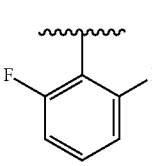 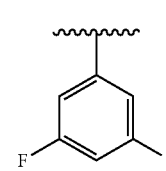 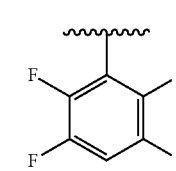

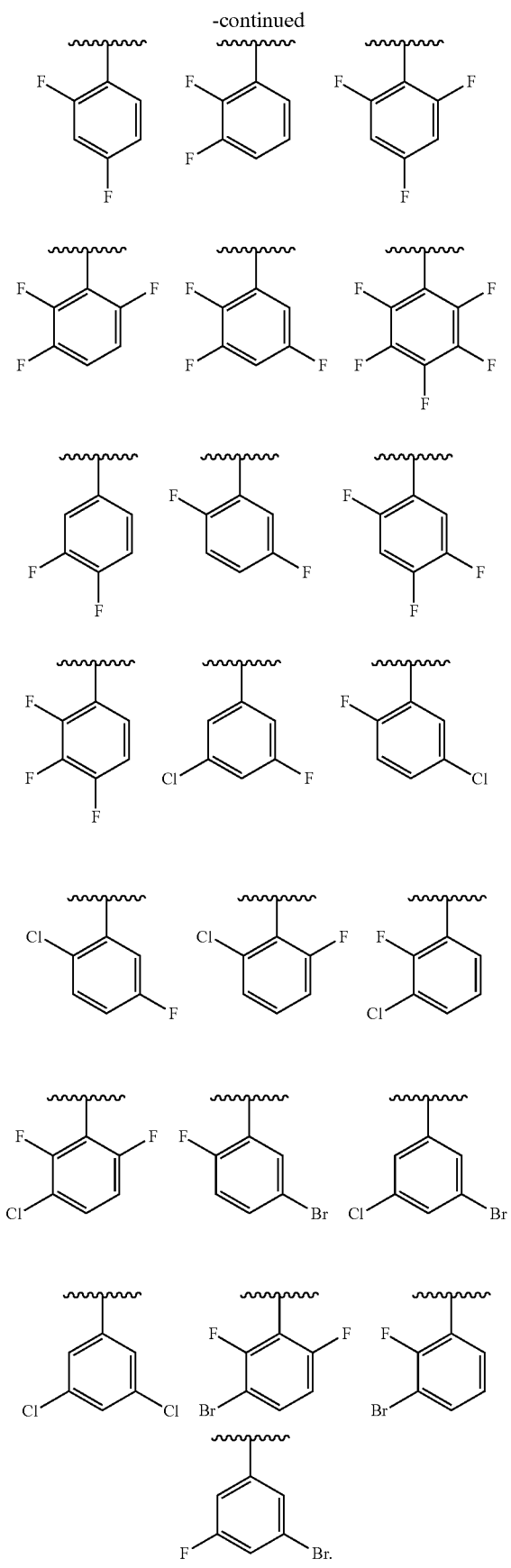

The following compounds represent specific embodiments of the invention:

(5aS,6aR)-5a-(2,5-difluorophenyl)-1-methyl-5,5a,6,6a-tetrahydrocyclopropa[3,4]pyrrolo[1,2-c]imidazole-3(2H)-thione;

(5aS,6aR)-5a-(3,5-difluorophenyl)-1-methyl-5,5a,6,6a-tetrahydrocyclopropa[3,4]pyrrolo[1,2-c]imidazole-3(2H)-thione;

(S)-1-butyl-6-(3,5-difluorophenyl)-6,7-dihydro-2H-pyrrolo[1,2-c]imidazole-3(5H)-thione;

(S)-6-(3,5-difluorophenyl)-1-methyl-2,5,6,7-tetrahydro-3H-pyrrolo[1,2-c]imidazole-3-thione;

(R)-1-methyl-6-(2,3,5,6-tetrafluorophenyl)-2,5,6,7-tetrahydro-3H-pyrrolo[1,2-c]imidazole-3-thione;

(S)-1-methyl-6-(2,3,5,6-tetrafluorophenyl)-2,5,6,7-tetrahydro-3H-pyrrolo[1,2-c]imidazole-3-thione;

(S)-6-(2,6-difluorophenyl)-1-methyl-2,5,6,7-tetrahydro-3H-pyrrolo[1,2-c]imidazole-3-thione;

(5aS,6aR)-5a-(5-chloro-2-fluorophenyl)-1-methyl-5,5a,6,6a-tetrahydrocyclopropa[3,4]pyrrolo[1,2-c]imidazole-3(2H)-thione;

(5aS,6aR)-5a-(5-chloro-2-fluorophenyl)-1-(methyl-$d_3$)-5,5a,6,6a-tetrahydrocyclopropa[3,4]pyrrolo[1,2-c]imidazole-3(2H)-thione;

(R)-6-(3-chloro-2,6-difluorophenyl)-1-methyl-2,5,6,7-tetrahydro-3H-pyrrolo[1,2-c]imidazole-3-thione;

(S)-6-(3-chloro-2,6-difluorophenyl)-1-methyl-2,5,6,7-tetrahydro-3H-pyrrolo[1,2-c]imidazole-3-thione;

(5aS,6aR)-5a-(3-bromo-2,6-difluorophenyl)-1-methyl-5,5a,6,6a-tetrahydrocyclopropa[3,4]pyrrolo[1,2-c]imidazole-3(2H)-thione;

(5aS,6aR)-5a-(5-bromo-2-fluorophenyl)-1-methyl-5,5a,6,6a-tetrahydrocyclopropa[3,4]pyrrolo[1,2-c]imidazole-3(2H)-thione;

(5aS,6aR)-5a-(3-chloro-2,6-difluorophenyl)-1-methyl-5,5a,6,6a-tetrahydrocyclopropa[3,4]pyrrolo[1,2-c]imidazole-3(2H)-thione;

(R)-6-(3-bromo-2,6-difluorophenyl)-1-methyl-2,5,6,7-tetrahydro-3H-pyrrolo[1,2-c]imidazole-3-thione;

(S)-6-(3-bromo-2,6-difluorophenyl)-1-methyl-2,5,6,7-tetrahydro-3H-pyrrolo[1,2-c]imidazole-3-thione;

(5aS,6aR)-5a-(3-chloro-5-fluorophenyl)-1-methyl-5,5a,6,6a-tetrahydrocyclopropa[3,4]pyrrolo[1,2-c]imidazole-3(2H)-thione;

(5aS,6aR)-5a-(5-bromo-2-fluorophenyl)-1-(methyl-$d_3$)-5,5a,6,6a-tetrahydrocyclopropa[3,4]pyrrolo[1,2-c]imidazole-3(2H)-thione;

(S)-6-(5-bromo-2-fluorophenyl)-1-methyl-2,5,6,7-tetrahydro-3H-pyrrolo[1,2-c]imidazole-3-thione;

(R)-1-methyl-6-(2,3,6-trifluorophenyl)-6,7-dihydro-2H-pyrrolo[1,2-c]imidazole-3(5H)-thione;

(R)-6-(5-bromo-2-fluorophenyl)-1-methyl-2,5,6,7-tetrahydro-3H-pyrrolo[1,2-c]imidazole-3-thione;

(R)-6-(2,6-difluorophenyl)-1-methyl-2,5,6,7-tetrahydro-3H-pyrrolo[1,2-c]imidazole-3-thione;

(R)-6-(5-chloro-2-fluorophenyl)-1-methyl-2,5,6,7-tetrahydro-3H-pyrrolo[1,2-c]imidazole-3-thione; and (S)-6-(5-chloro-2-fluorophenyl)-1-methyl-2,5,6,7-tetrahydro-3H-pyrrolo[1,2-c]imidazole-3-thione.

C. Compositions

The compounds of the invention intended for pharmaceutical use may be administered alone or in combination with one or more other compounds of the invention or in combination with one or more other drugs (or as any combination thereof). Generally, they will be administered as a formulation in association with one or more pharmaceutically acceptable excipients. Accordingly, the present invention is also directed to a pharmaceutical composition comprising (i) a therapeutically effective amount of a compound of formula Ia, as defined above, or a pharmaceutically acceptable salt or solvate thereof; and (ii) a pharmaceutically acceptable excipient.

Pharmaceutical compositions suitable for the delivery of compounds of the present invention and methods for their preparation will be readily apparent to those skilled in the art. Such compositions and methods for their preparation may be found, for example, in "Remington's Pharmaceutical Sciences", 19th Edition (Mack Publishing Company, 1995).

D. Methods of Use

This invention is also directed to compounds of formula Ia, as defined above, or a pharmaceutically acceptable salt or solvate thereof, for use in therapy, in particular for the treatment of conditions ameliorated by inhibition of DβH.

This invention is also directed to the use of compounds of formula Ia, as defined above, or a pharmaceutically acceptable salt or solvate thereof, in the manufacture of a medicament for treatment of conditions ameliorated by inhibition of DβH.

This invention is also directed to a method for treating conditions ameliorated by inhibition of dopamine-beta-hydroxylase comprising administering a therapeutically effective amount of a compound of formula Ia, as defined above, or a pharmaceutically acceptable salt or solvate thereof, to a patient in need thereof.

Conditions ameliorated by inhibition of DβH outside the CNS can include, but are not limited to: cardiovascular disorders such as hypertension, chronic heart failure and pulmonary arterial hypertension (PAH).

Conditions ameliorated by inhibition of DβH within the CNS can include, but are not limited to: cocaine addiction, alcohol addiction, adjunct opioid addiction, cognition decline in FTD, cognition decline in MCI, cognition decline in AD, ADHD, PTSD and unipolar depression.

E. General Synthetic Methodology

The methods used for the synthesis of the compounds of the invention are illustrated by the schemes below. The starting materials and reagents used in preparing these compounds are available from commercial suppliers or can be prepared by methods obvious to those skilled in the art. To make the schemes easier to read, the option to incorporate deuterium at certain positions is not shown. Specifically, deuterated products can be produced using specifically deuterated starting materials, including, but not limited to, those used in the Examples below.

Compounds of formula Ia can generally be synthesised by the method outlined in Scheme 1:

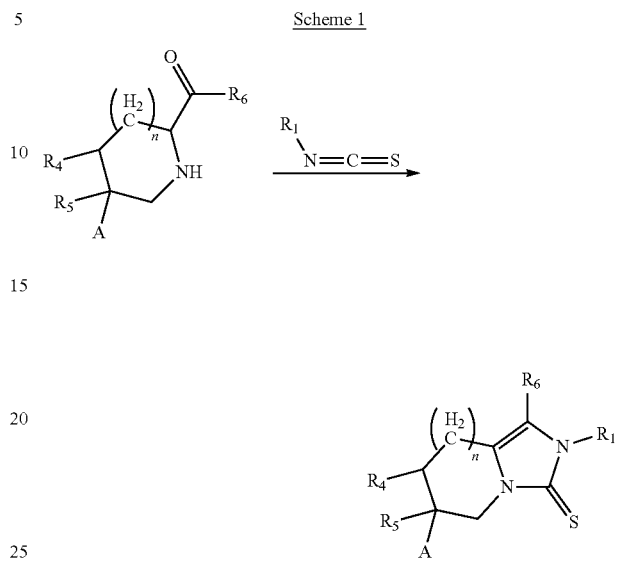

The starting material in Scheme 1 can generally be synthesised by the method outlined in Scheme 2:

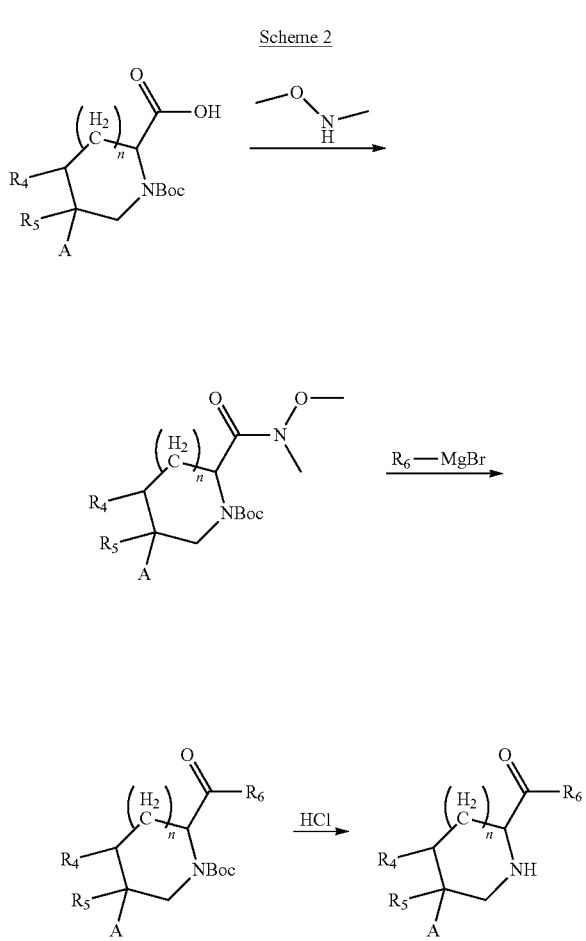

The starting material for Scheme 2, when n=0, can generally be synthesised by the method outlined in Scheme 3 as either enriched enantiomers or racemates:

Scheme 3

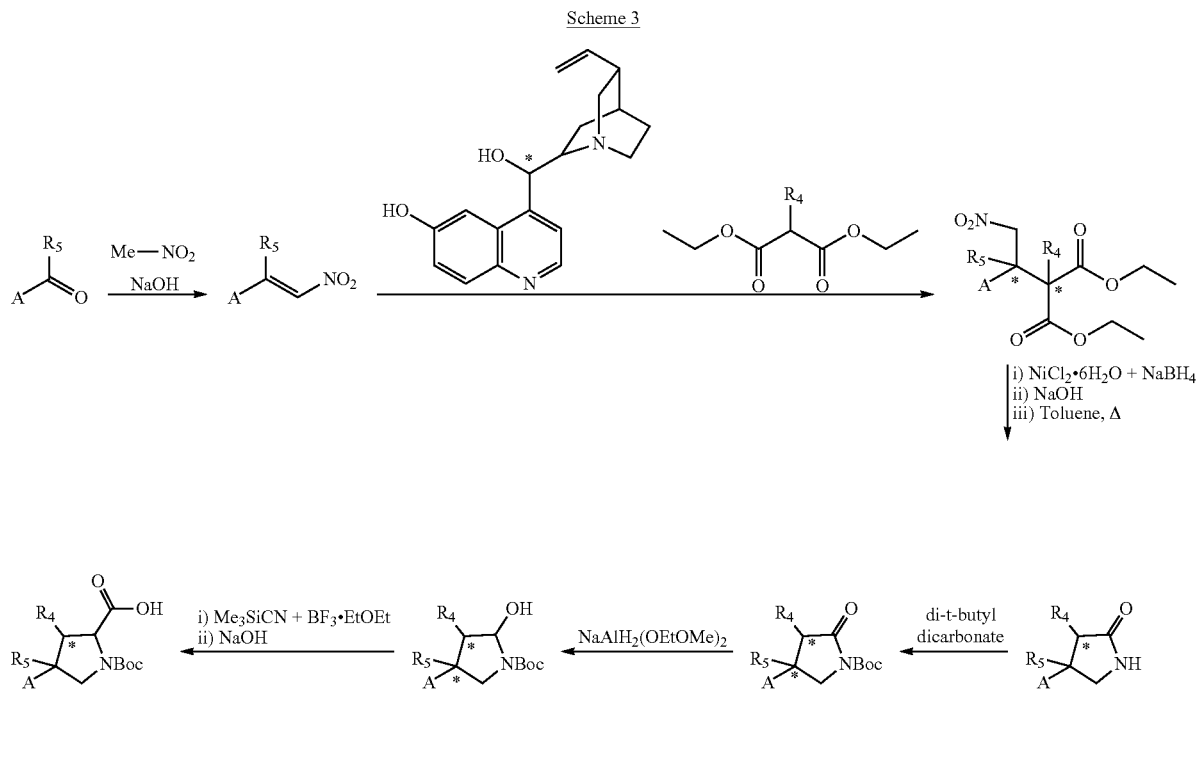

When $R_4$ and $R_5$ combine to form a cyclopropyl group, the starting material in Scheme 1 can generally be synthesised by the method outlined in Scheme 4:

Scheme 4

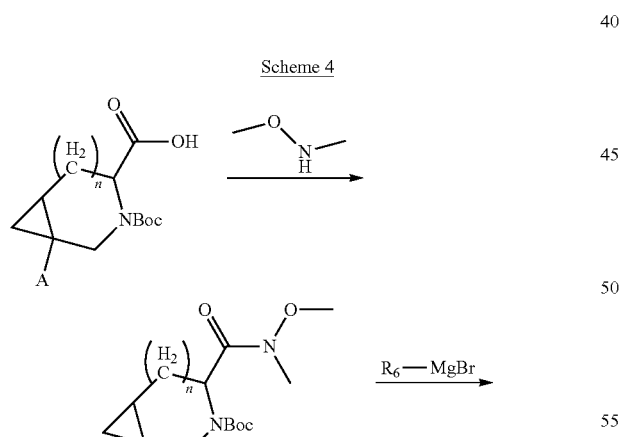

The starting material for Scheme 4 can generally be synthesised by the method outlined in Scheme 5:

Scheme 5

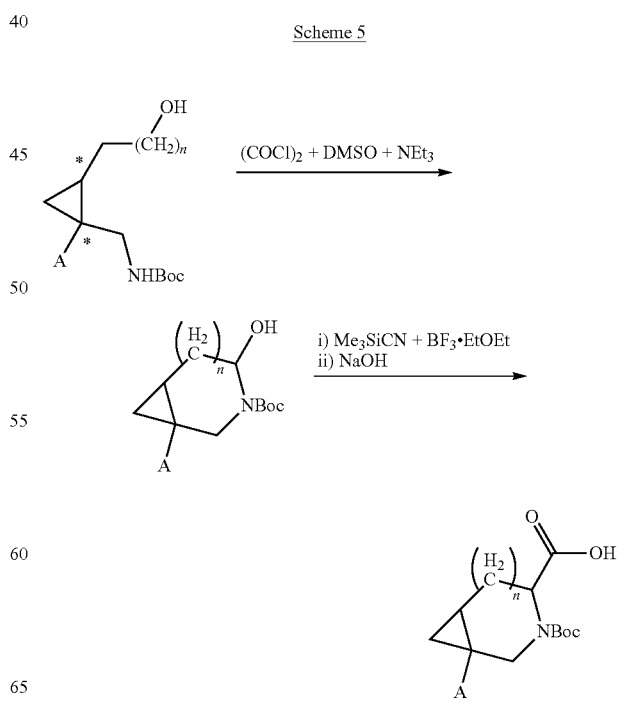

In turn, the starting material for Scheme 5 can generally be synthesised by the method outlined in Scheme 6 as either enriched enantiomers or racemates and including specific deuteration:

Scheme 6

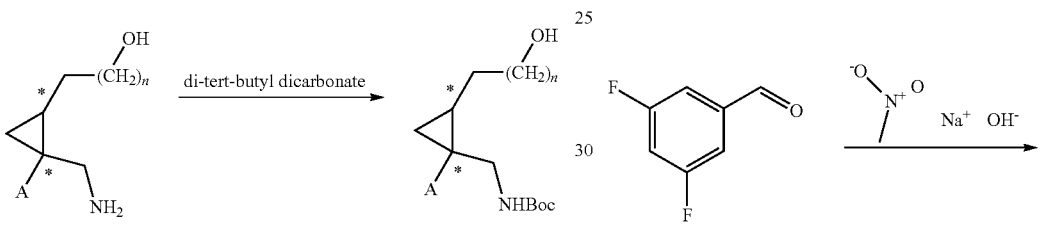

In accordance with this synthetic methodology, the invention provides a process for the preparation of compounds of formula Ia

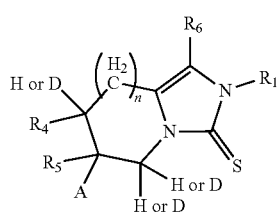
(Ia)

which comprises reacting a compound of formula IIa wherein n, $R_4$, $R_5$, $R_6$ and A are as defined for formula Ia above

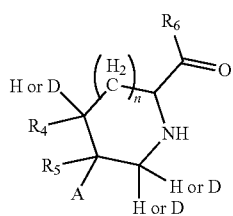
(IIa)

with a compound of formula $R^1$—N═C═S.

Compounds of formula IIa wherein n, $R_4$, $R_5$, $R_6$ and A are as defined for formula Ia above are thus useful intermediates representing further embodiments of the present invention.

F. Examples

All compounds and intermediates were characterised by NMR. The spectra were recorded on a Bruker Avance III 600 MHz spectrometer with solvent used as internal standard. $^{13}C$ spectra were recorded at 150 MHz and $^1H$ spectra were recorded at 600 MHz. Data are reported in the following order: approximate chemical shift (ppm), number of protons, multiplicity (br, broad; d, doublet; m, multiplet; s, singlet; t, triplet) and coupling constant (Hz).

Room temperature in the following protocols means the temperature ranging from 20° C. to 25° C.

Preparative Example 1

Step 1: (E)-1,3-difluoro-5-(2-nitrovinyl)benzene

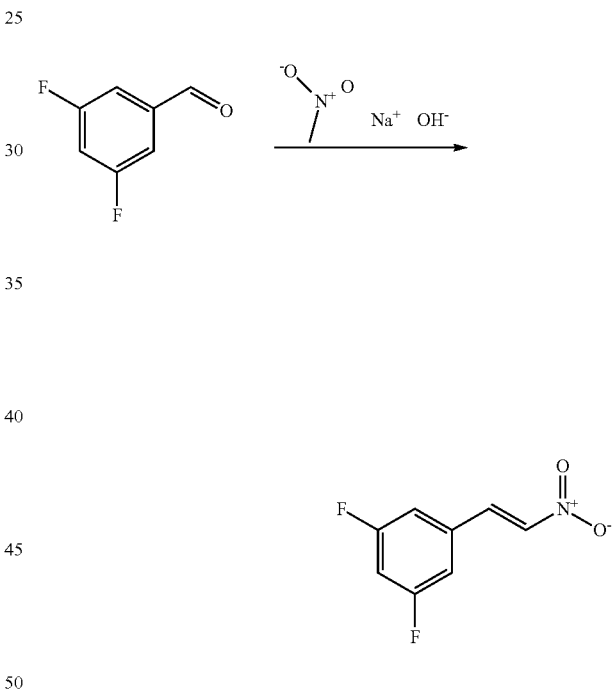

To a solution of methanol (72 mL), water (36 mL), and 2.5 M sodium hydroxide (32.4 mL, 81 mmol) was added a solution of 3,5-difluorobenzaldehyde (10 g, 70.4 mmol) and nitromethane (4.36 mL, 81 mmol) in methanol (12.00 mL) dropwise over 30 min at 5° C., while the internal temperature was maintained between 5 and 10° C. with external cooling. The reaction was then agitated in the cold for an additional 0.5 h, and then a solution of cc. HCl (11.73 mL, 141 mmol) in water (36 mL) was added in one portion at 0-10° C. with stirring. The resulting crystals were collected, washed with water and dried to give the product as a light yellow powder. (Yield: 7.0 g, 54%).

Step 2: (R)-diethyl 2-(1-(3,5-difluorophenyl)-2-nitroethyl)malonate

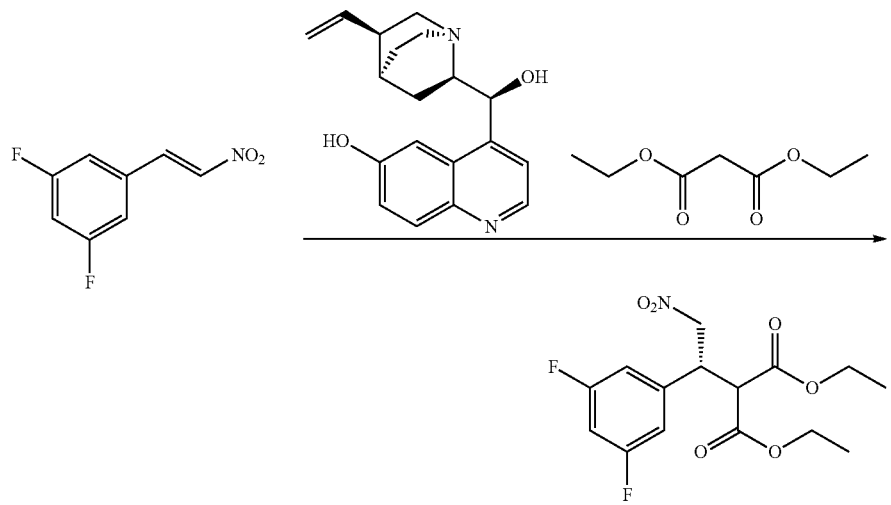

To a stirred solution of (E)-1,3-difluoro-5-(2-nitrovinyl)benzene (7.4 g, 40.0 mmol) in dry tetrahydrofuran (75 mL) was added 4-((S)-hydroxy((1S,2R,4S,5R)-5-vinylquinuclidin-2-yl)methyl)quinolin-6-ol (CAS #70877-75-7) (0.620 g, 1.999 mmol) at room temperature with stirring followed by addition of diethyl malonate (8.65 mL, 56.7 mmol). The mixture was cooled to −5 to −7° C. under inert atmosphere and stirred for 20 h in the cold. Thereupon, the mixture was evaporated to dryness under vacuum and the residue was taken up in dichloromethane (100 mL), washed with 1 M HCl, brine, dried over MgSO$_4$ and filtered on a silica pad. The filtrate was concentrated to 20 mL, and the residue was crystallized on dilution with petroleum ether (ca. 50 mL). The mixture was further diluted with petroleum ether (120 mL), and aged at 5-10° C. The resulting solid was collected, washed with petroleum ether, and dried to give the product as an off-white powder. (Yield: 9.1 g, 70%).

Step 3: (4R)-ethyl 4-(3,5-difluorophenyl)-2-oxopyrrolidine-3-carboxylate

To a suspension of (R)-diethyl 2-(1-(3,5-difluorophenyl)-2-nitroethyl)malonate (9 g, 26.1 mmol) in methanol (150 mL) was added nickel(II) chloride hexahydrate (6.20 g, 26.1 mmol) followed by addition of sodium borohydride (7.89 g, 209 mmol) in portions with ice cooling. The mixture was stirred for 6 h at room temperature, then quenched with ammonium chloride solution (250 mL), diluted with dichloromethane (150 mL), acidified with 6 M HCl to pH=2, and stirred for 16 h. Thereupon, the mixture was extracted with dichloromethane, the organic phase was dried over MgSO$_4$ and evaporated to dryness to give the product as a beige powder. (Yield: 6.87 g, 98%).

Step 4: (4R)-4-(3,5-difluorophenyl)-2-oxopyrrolidine-3-carboxylic acid

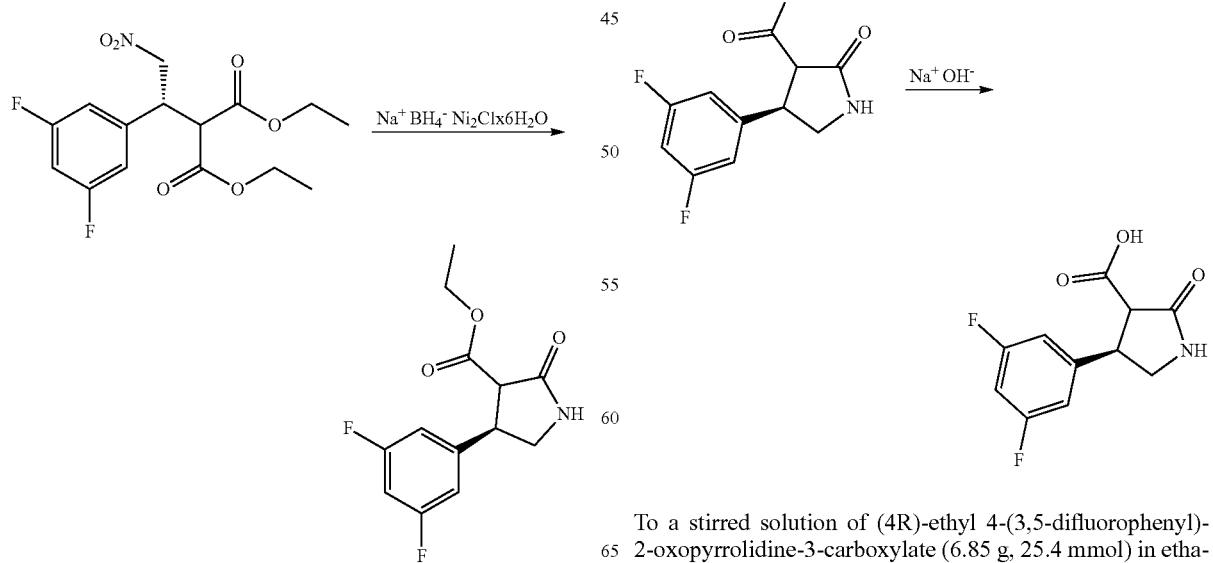

To a stirred solution of (4R)-ethyl 4-(3,5-difluorophenyl)-2-oxopyrrolidine-3-carboxylate (6.85 g, 25.4 mmol) in ethanol (100 mL) was added 1 M sodium hydroxide (30.5 mL, 30.5 mmol). The resulting suspension was stirred for 1 h, the organics were then removed under vacuum, and the residue was dissolved in water (250 mL). The product was crystallized on acidification with 6 M HCl. The resulting crystals were collected, washed with cold water and dried under vacuum at 50° C. to give the product as a beige powder Yield: 5.2 g, 21, 85%.

Step 5: (R)-4-(3,5-difluorophenyl)pyrrolidin-2-one

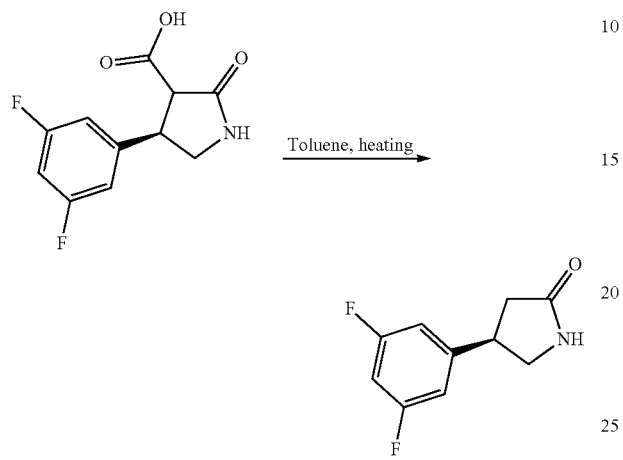

A solution of (4R)-4-(3,5-difluorophenyl)-2-oxopyrrolidine-3-carboxylic acid (5.2 g, 21.56 mmol) in toluene (300 mL) was stirred under reflux for 3 h, whereupon the mixture was evaporated to dryness, Crystallization from petroleum ether afforded beige powder. Yield: 4.06 g, 96%.

Step 6: (R)-tert-butyl 4-(3,5-difluorophenyl)-2-oxopyrrolidine-1-carboxylate

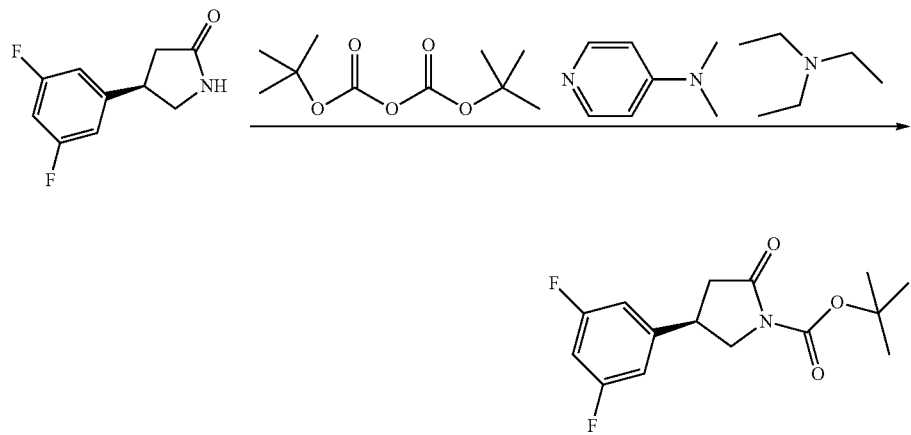

To a stirred solution of (R)-4-(3,5-difluorophenyl)pyrrolidin-2-one (4.05 g, 20.54 mmol) in dry dichloromethane (15 mL) was added at room temperature di-tert-butyl dicarbonate (6.72 g, 30.8 mmol) followed by addition of N,N-dimethylpyridin-4-amine (2.509 g, 20.54 mmol) and triethyl amine (2.86 mL, 20.54 mmol). The mixture was then stirred at room temperature for 3 h, and then concentrated under vacuum. Chromatography (petroleum ether—ethyl acetate; 4:1) gave an oil which was crystallized from petroleum ether (60 mL), The product was isolated as a white powder. Yield: 6.24 g, 88%.

Step 7: (4R)-tert-butyl 4-(3,5-difluorophenyl)-2-hydroxy-pyrrolidine-1-carboxylate

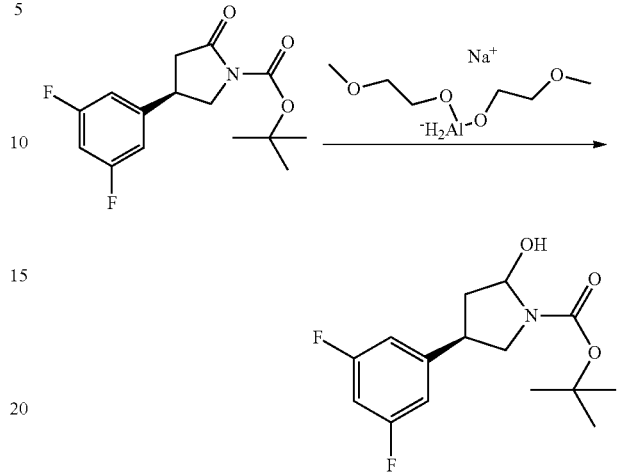

To a stirred solution of (R)-tert-butyl 4-(3,5-difluorophenyl)-2-oxopyrrolidine-1-carboxylate (2 g, 6.73 mmol) in dry diethyl ether (30 mL) was added dropwise 65% RED-Al (bis(2-methoxyethoxy)aluminum(III) sodium hydride) (1.212 mL, 4.04 mmol) in toluene at 0-5° C. under nitrogen and the mixture was stirred for 30 min. in the cold. Thereupon, the mixture was quenched with sodium bicarbonate solution and stirred for 30 min. The organic phase was dried over MgSO$_4$, and evaporated to dryness to give the product as colourless oil. (Yield: 2.07 g, 93%).

Step 8: (4R)-tert-butyl 2-cyano-4-(3,5-difluorophenyl)pyrrolidine-1-carboxylate

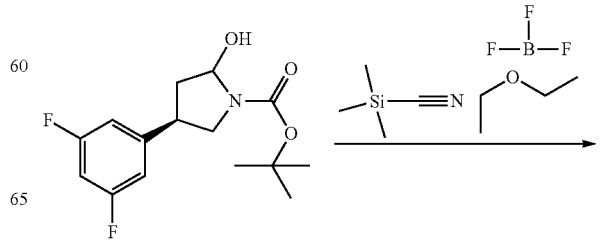

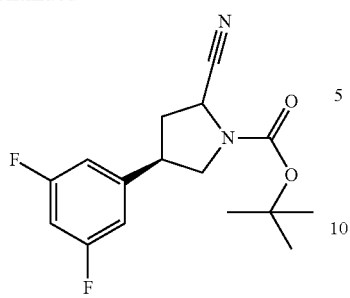

To a stirred solution of (4R)-tert-butyl 4-(3,5-difluorophenyl)-2-hydroxypyrrolidine-1-carboxylate (2 g, 6.68 mmol) in dry dichloromethane (50 mL) was added trimethylsilanecarbonitrile (1.792 mL, 13.36 mmol) followed by addition of boron trifluoride etharate (1.863 mL, 14.70 mmol) at −70° C. The mixture was stirred for 4 h in the cold, quenched with sodium bicarbonate solution, and then allowed to warm up with stirring to room temperature. The organic phase was dried over MgSO$_4$, filtered and evaporated to dryness under vacuum. Chromatography (petroleum ether—ethyl acetate; 9:1) afforded the compound as a colourless oil. (Yield: 1.36 g, 66%).

Step 9: (4R)-1-(tert-butoxycarbonyl)-4-(3,5-difluorophenyl)pyrrolidine-2-carboxylic acid

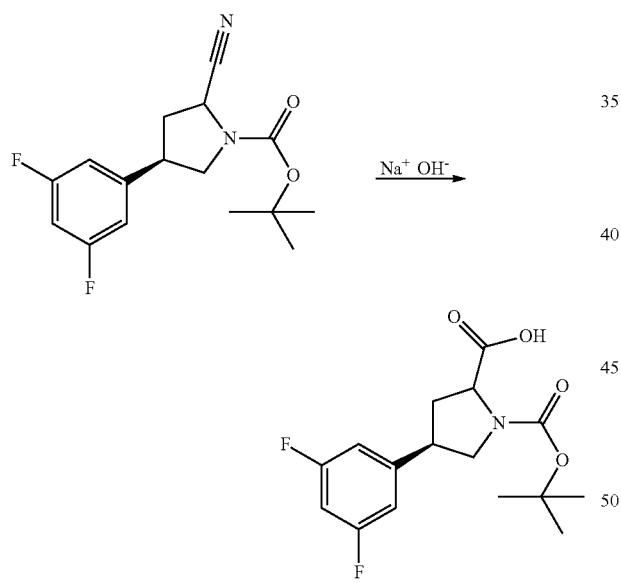

To a stirred solution of (4R)-tert-butyl 2-cyano-4-(3,5-difluorophenyl)pyrrolidine-1-carboxylate (1.35 g, 4.38 mmol) in ethanol (15 mL) was added 3 M sodium hydroxide (7.30 mL, 21.89 mmol) and the solution was gently refluxed (oil bath at 80° C.) for 3 h. Thereupon, ethanol was removed under vacuum and the residue was diluted with water (10 mL), and then acidified with 2 M HCl to pH=2 at 10-15° C. The mixture was extracted with dichloromethane (40 mL), the insoluble materials in both phases was filtered off, whereupon the organic phase was washed with brine, dried over MgSO$_4$ and evaporated to dryness to give 0.89 g of yellowish oil. (Yield: 62%).

Example 1: (5aS,6aR)-5a-(2,5-difluorophenyl)-1-methyl-5,5a,6,6a-tetrahydrocyclopropa[3,4]pyrrolo[1,2-c]imidazole-3(2H)-thione

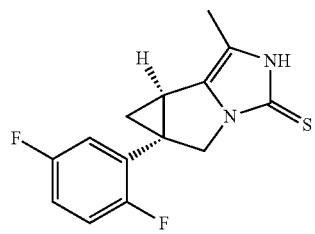 [SMILES: Cc1[nH]c(=S)n2c1[C@@H]1C[C@]1(c1cc(F)ccc1F)C2]

Compound was prepared in an analogous manner to Example 3 from (5S)-3-(tert-butoxycarbonyl)-5-(2,5-difluorophenyl)-3-azabicyclo[3.1.0]hexane-2-carboxylic acid and methylmagnesium iodide and isolated as a yellow solid.

$^1$H NMR (DMSO-d6): 11.66 (1H, br s), 7.28 (2H, m), 7.20 (1H, m), 4.06 (1H, d, J=12.0 Hz), 3.78 (1H, d, J=12.0 Hz), 2.86 (1H, dd, J=8.2, 4.3 Hz), 2.09 (1H, m), 2.04 (3H, s), 1.63 (1H, dd, J=8.1, 5.4 Hz), 1.13 (1H, t, J=4.8 Hz).

$^{13}$C NMR (DMSO-d6): 158.8, 158.7, 157.2, 157.1, 155.7, 130.3, 128.8, 128.8, 128.8, 128.7, 128.6, 117.2, 117.1, 117.0, 116.9, 116.8, 115.9, 115.8, 115.7, 115.7, 114.8, 51.5, 32.5, 22.4, 20.3, 9.4.

Example 2: (5aS,6aR)-5a-(3,5-difluorophenyl)-1-methyl-5,5a,6,6a-tetrahydrocyclopropa[3,4]pyrrolo[1,2-c]imidazole-3(2H)-thione

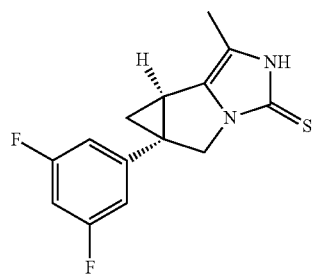 [SMILES: Cc1[nH]c(=S)n2c1[C@@H]1C[C@]1(c1cc(F)cc(F)c1)C2]

Compound was prepared in an analogous manner to Example 3 from (5S)-3-(tert-butoxycarbonyl)-5-(3,5-difluorophenyl)-3-azabicyclo[3.1.0]hexane-2-carboxylic acid and methylmagnesium iodide and isolated as a yellow solid.

$^1$H NMR (DMSO-d6): 1.63 (1H, br s), 7.10 (3H, m), 4.17 (1H, d, J=12.0 Hz), 4.00 (1H, d, J=12.2 Hz), 2.97 (1H, dd, J=8.3, 4.3 Hz), 2.03 (3H, s), 1.65 (1H, dd, J=8.2, 5.1 Hz), 1.15 (1H, m).

$^{13}$C NMR (DMSO-d6): 163.4, 163.3, 161.8, 161.7, 156, 145, 130.2, 114.5, 110, 110, 109.9, 109.9, 102.1, 50.7, 36.1, 25.4, 22.4, 9.4.

Example 3: (S)-1-butyl-6-(3,5-difluorophenyl)-6,7-dihydro-2H-pyrrolo[1,2-c]imidazole-3(5H)-thione Step 1: (4S)-tert-butyl 4-(3,5-difluorophenyl)-2-(methoxy(methyl)carbamoyl)pyrrolidine-1-carboxylate

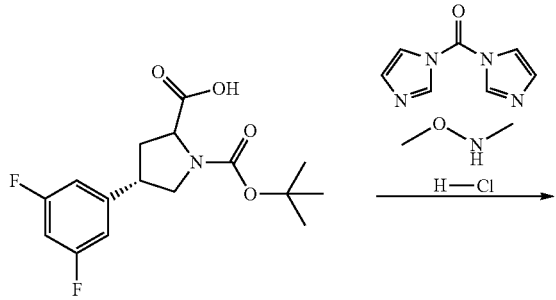

To a solution of (4S)-1-(tert-butoxycarbonyl)-4-(3,5-difluorophenyl)pyrrolidine-2-carboxylic acid (prepared in a manner analogous to Preparative Example 1, step 9) (0.982 g, 3 mmol) in dry dichloromethane (10 mL) was added di(1H-imidazol-1-yl)methanone (0.584 g, 3.60 mmol) in portions at room temperature and the mixture was stirred for 30 min. Thereupon, N,O-dimethylhydroxylamine hydrochloride (0.351 g, 3.60 mmol) was added and the stirring was continued at room temperature for 40 h. The reaction was then washed with water, the organic phase was dried over MgSO₄ and concentrated under vacuum. Chromatography (petroleum ether—ethyl acetate; 2:1) afforded the product as an off-white solid. (Yield: 0.92 g, 83%).

Step 2: tert-butyl (4S)-4-(3,5-difluorophenyl)-2-pentanoylpyrrolidine-1-carboxylate

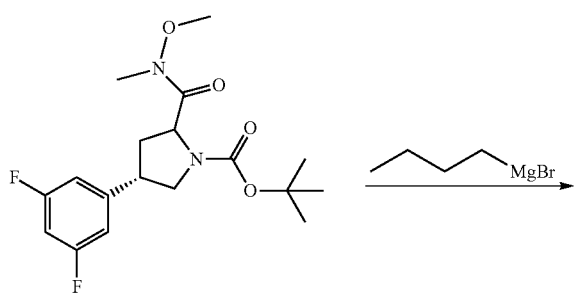

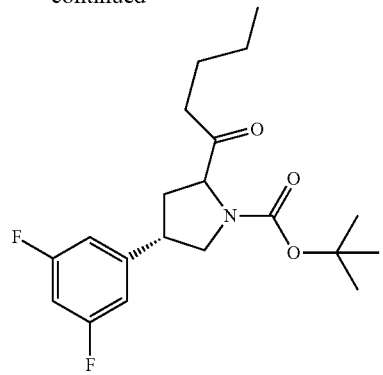

To a solution of (4S)-tert-butyl 4-(3,5-difluorophenyl)-2-(methoxy(methyl)carbamoyl)pyrrolidine-1-carboxylate (0.40 g, 1.08 mmol) in dry tetrahydrofuran (2 mL) was added 2 M butylmagnesium bromide (1.62 mL, 3.24 mmol) at 0-5° C. under nitrogen. The mixture was allowed to warm up to room temperature and stirred for 3 h. Thereupon, the mixture was poured onto 1 M HCl and then extracted with diethyl ether. The organic phase was washed with brine, dried over MgSO₄, and evaporated to dryness. Chromatography (petroleum ether—ethyl acetate; 9:1) afforded the product as a colourless oil. (Yield: 0.2 g, 50%).

Step 3: (S)-1-benzyl-6-(3,5-difluorophenyl)-6,7-dihydro-2H-pyrrolo[1,2-c]imidazole-3(5H)-thione

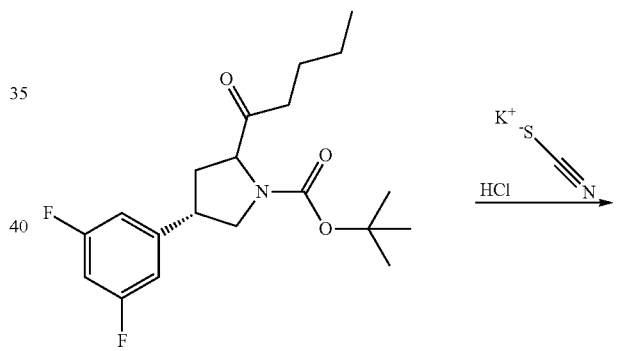

A mixture of (4S)-tert-butyl 4-(3,5-difluorophenyl)-2-pentanoylpyrrolidine-1-carboxylate (0.19 g, 0.517 mmol) and 4 M HCl (2.59 mL, 10.34 mmol) in dioxane was stirred at room temperature overnight. The mixture was then cooled to room temperature and evaporated to dryness. The thus obtained oily residue was dissolved in a mixture of ethanol (2 mL) and water (2 mL), followed by addition of potassium thiocyanate (0.055 g, 0.569 mmol) and 6 M HCl (0.043 mL, 0.259 mmol). The mixture was stirred under reflux for 1 h, then stirred at room temperature for 30 min. The obtained solid was collected by filtration, washed with a mixture of ethanol water (1:1) and dried under vacuum at 50° C. to give the product as a light beige powder. (Yield: 0.12 g, 75%).
¹H NMR (DMSO-d6): 11.71 (1H, s), 7.13 (3H, m), 4.14 (1H, dd, J=11.2, 7.9 Hz), 4.07 (1H, quin, J=8.1 Hz), 3.67 (1H, dd, J=11.1, 8.3 Hz), 3.20 (1H, dd, J=15.0, 7.8 Hz), 2.84 (1H, dd, J=15.1, 8.8 Hz), 2.35 (2H, t, J=7.5 Hz), 1.50 (2H, m), 1.26 (2H, m), 0.86 (3H, t, J=7.4 Hz).
¹³C NMR (DMSO-d6): 163.3, 163.2, 161.7, 161.6, 155.1, 145.8, 145.7, 145.6, 127.6, 120, 110.8, 110.7, 110.6, 110.6, 102.6, 102.5, 102.3, 49.9, 46.5, 30.4, 29.8, 23.6, 21.5, 13.6.
Example 4: (S)-6-(3,5-difluorophenyl)-1-methyl-2,5,6,7-tetrahydro-3H-pyrrolo[1,2-c]imidazole-3-thione
Step 1: ((4S)-tert-butyl 2-(cyano(hydroxy)methyl)-4-(3,5-difluorophenyl)pyrrolidine-1-carboxylate

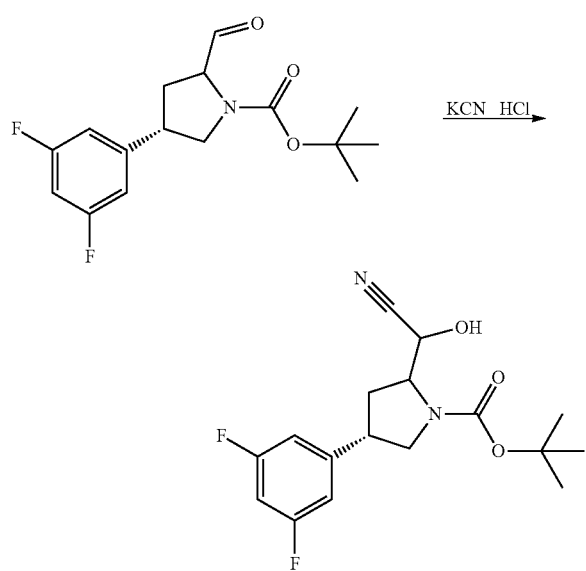

To a stirred solution of (4S)-tert-butyl 4-(3,5-difluorophenyl)-2-formylpyrrolidine-1-carboxylate (1.2 g, 3.85 mmol) in a mixture of tetrahydrofuran (10 mL) and water (5 mL) was added potassium cyanide (0.301 g, 4.63 mmol) followed by addition of cc HCl (0.319 mL, 3.85 mmol). The mixture was stirred for 8 h, then extracted with dichloromethane. The organic phase was washed with brine, dried over MgSO₄ and evaporated to dryness to give (4S)-tert-butyl 2-(cyano(hydroxy)methyl)-4-(3,5-difluorophenyl)pyrrolidine-1-carboxylate as a yellowish oil. (Yield: 1.44 g, 99%).
Step 2: (4S)-tert-butyl 4-(3,5-difluorophenyl)-2-(2-ethoxy-1-hydroxy-2-oxoethyl)pyrrolidine-1-carboxylate

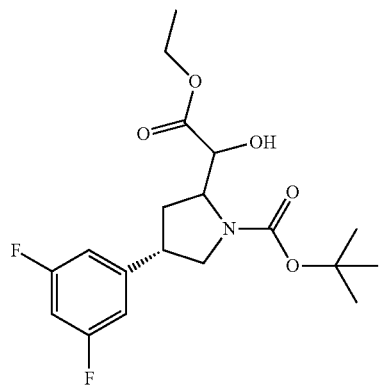

A mixture of (4S)-tert-butyl 2-(cyano(hydroxy)methyl)-4-(3,5-difluorophenyl)pyrrolidine-1-carboxylate (1.43 g, 3.80 mmol) and 2 M HCl (28.5 mL, 57.1 mmol) was stirred under reflux for 16 h. After cooling to room temperature the mixture was filtered through a celite plug to remove insoluble coloured precipitate and then the filtrate was evaporated to dryness under vacuum. The residue was azeotroped twice with dry ethanol and the residue was taken up in abs. ethanol (20 mL). The thus obtained solution was treated with 4 M HCl (9.51 mL, 38.0 mmol) in dioxane and stirred under reflux for 2 h. The mixture was evaporated to dryness, and then azeotroped with abs. ethanol. The resulting semi-solid was taken up in abs. ethanol (30 mL), neutralized by addition of triethylamine to pH=6-7, then a second crop of triethylamine (0.530 mL, 3.80 mmol) was added followed by addition of di-tert-butyl dicarbonate (0.830 g, 3.80 mmol). The reaction was allowed to stir at room temperature for 2 h, and then evaporated to dryness at 40° C. The residue was partitioned between dichloromethane and water, the organic phase was dried over MgSO₄ and concentrated under reduced pressure. Chromatography (petroleum ether—ethyl acetate; 9:1, then 4:1) gave the product as a yellow oil. (Yield: 1.16 g, 79%).
Step 3: (4S)-tert-butyl 4-(3,5-difluorophenyl)-2-(2-ethoxy-2-oxoacetyl)pyrrolidine-1-carboxylate

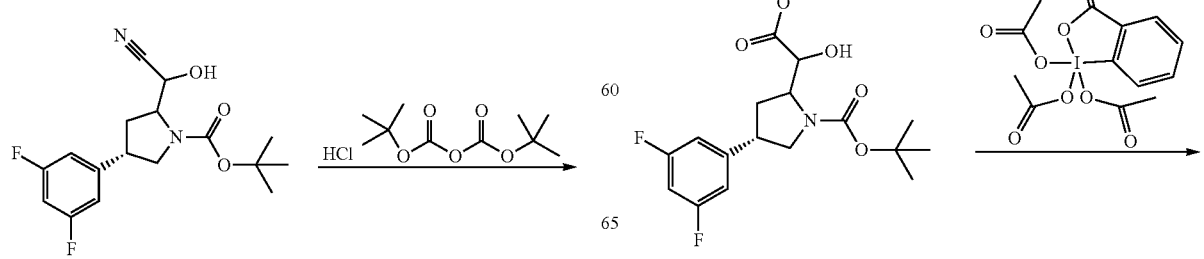

-continued

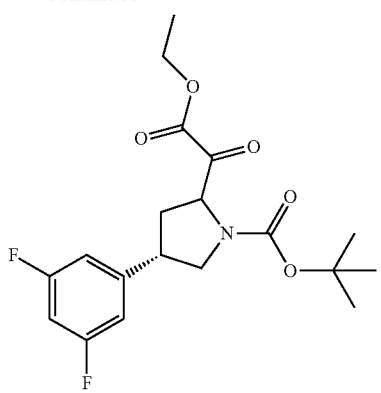

To a stirred solution of (4S)-tert-butyl 4-(3,5-difluorophenyl)-2-(2-ethoxy-1-hydroxy-2-oxoethyl)pyrrolidine-1-carboxylate (1.15 g, 2.98 mmol) in dry dichloromethane (25 mL) was added Dess-Martin periodinane (3-oxo-1λ$^5$-benzo[d][1,2]iodaoxole-1,1,1(3H)-triyl triacetate) (1.266 g, 2.98 mmol) at room temperature in one portion and the mixture was stirred for 2 h. The reaction mixture was concentrated under vacuum, whereupon the residue was purified by chromatography (petroleum ether—ethyl acetate; 4:1). The product was isolated as a yellowish oil. (1.08 g, 94% yield).

Step 4: ethyl 2-((4S)-4-(3,5-difluorophenyl)pyrrolidin-2-yl)-2-oxoacetate hydrochloride To a stirred solution of (4S)-tert-butyl 4-(3,5-difluorophenyl)-2-(2-ethoxy-2-oxoacetyl)pyrrolidine-1-carboxylate (0.4 g, 1.043 mmol) in 4 M HCl (5.22 mL, 20.87 mmol) in dioxane was stirred at room temperature for 4 h. The reaction mixture was diluted with a mixture of diethyl ether (20 mL) and petroleum ether (5 mL) and stirred for 30 min, Thereupon, the resulting precipitate was collected, washed with diethyl ether, petroleum ether and dried under vacuum at 50° C. to give ethyl 2-((4S)-4-(3,5-difluorophenyl)pyrrolidin-2-yl)-2-oxoacetate hydrochloride as a white powder. (Yield: 0.34 g, 92%).

Step 5: (S)-ethyl 6-(3,5-difluorophenyl)-3-thioxo-3,5,6,7-tetrahydro-2H-pyrrolo[1,2-c]imidazole-1-carboxylate

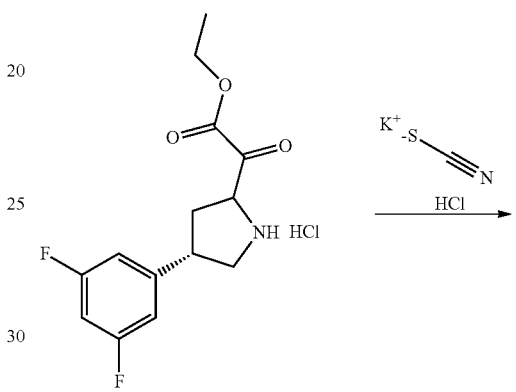

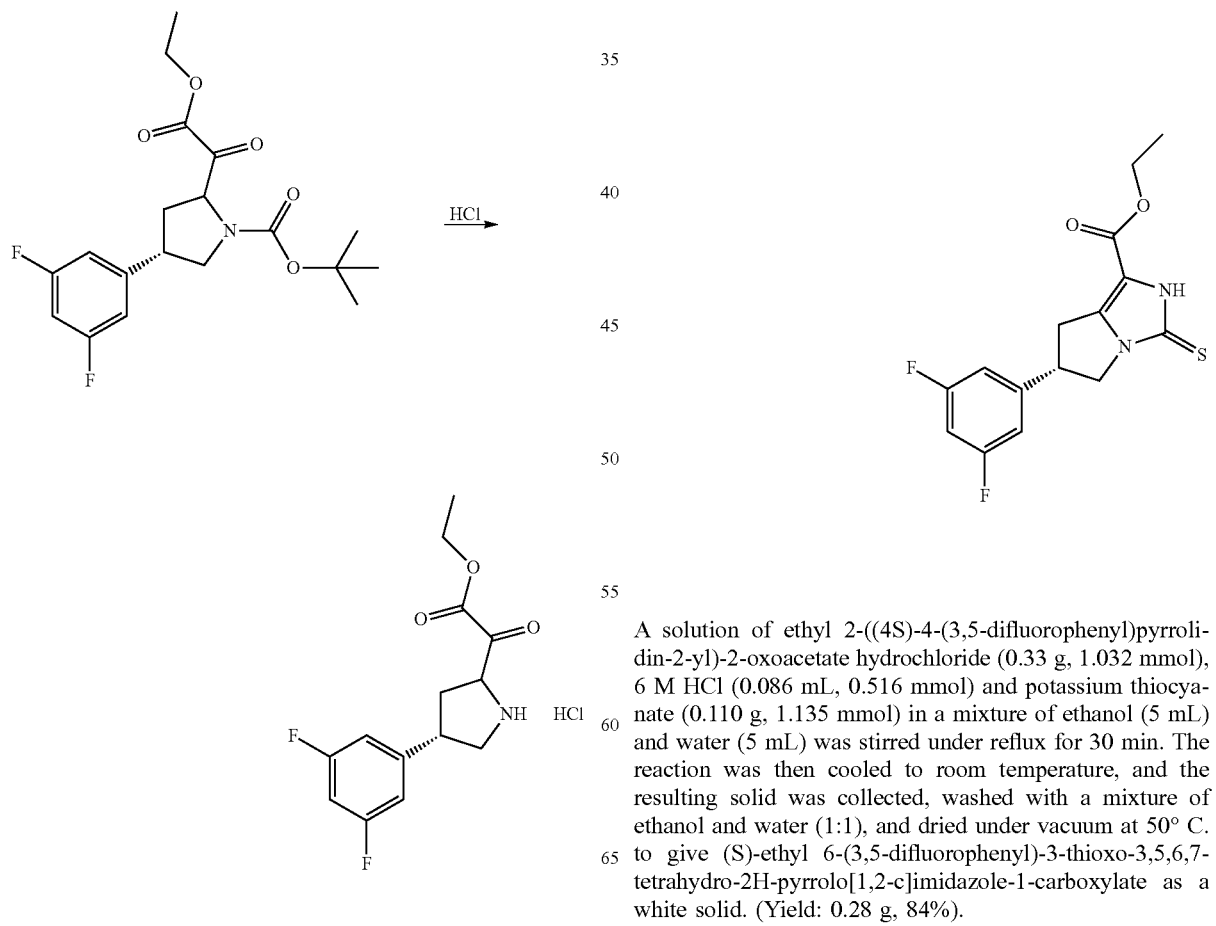

A solution of ethyl 2-((4S)-4-(3,5-difluorophenyl)pyrrolidin-2-yl)-2-oxoacetate hydrochloride (0.33 g, 1.032 mmol), 6 M HCl (0.086 mL, 0.516 mmol) and potassium thiocyanate (0.110 g, 1.135 mmol) in a mixture of ethanol (5 mL) and water (5 mL) was stirred under reflux for 30 min. The reaction was then cooled to room temperature, and the resulting solid was collected, washed with a mixture of ethanol and water (1:1), and dried under vacuum at 50° C. to give (S)-ethyl 6-(3,5-difluorophenyl)-3-thioxo-3,5,6,7-tetrahydro-2H-pyrrolo[1,2-c]imidazole-1-carboxylate as a white solid. (Yield: 0.28 g, 84%).

Step 6: S)-6-(3,5-difluorophenyl)-1-methyl-6,7-dihydro-2H-pyrrolo[1,2-c]imidazole-3(5H)-thione

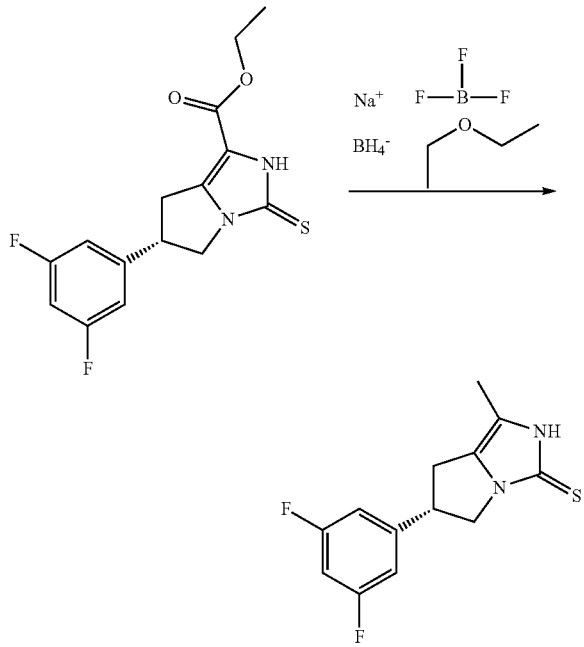

To a solution of (S)-ethyl 6-(3,5-difluorophenyl)-3-thioxo-3,5,6,7-tetrahydro-2H-pyrrolo[1,2-c]imidazole-1-carboxylate (0.1 g, 0.308 mmol) in dry tetrahydrofuran (2 mL) was added sodium borohydride (0.058 g, 1.542 mmol) followed by addition of boron trifluoride etherate (0.195 mL, 1.542 mmol) with ice-water bath cooling. The mixture was allowed to warm up to room temperature and stirred for 16 h. Thereupon, the mixture was cooled again to 0-5° C., and quenched with 2 M HCl (1.233 ml, 2.467 mmol). The organic solvents were removed under vacuum, and then the residue extracted with ethyl acetate. The organic phase was dried over MgSO$_4$, filtered and evaporated to dryness. Chromatography (petroleum ether—ethyl acetate; 1:1 gave (S)-6-(3,5-difluorophenyl)-1-methyl-6,7-dihydro-2H-pyrrolo[1,2-c]imidazole-3(5H)-thione as a white powder (0.021 g, 0.079 mmol, 25.6% yield).
$^1$H NMR (DMSO-d6): 11.69 (1H, br s), 7.13 (3H, m), 5.76 (1H, s), 4.15 (1H, dd, J=11.2, 7.9 Hz), 4.07 (1H, quin, J=7.8 Hz), 3.66 (1H, dd, J=11.2, 8.4 Hz), 3.18 (1H, m), 2.82 (1H, ddd, J=15.0, 8.9, 1.3 Hz), 1.98 (3H, s).
$^{13}$C NMR (DMSO-d6): 163.3, 163.2, 161.7, 161.6, 155.1, 145.7, 145.7, 145.6, 127.8, 115.4, 110.8, 110.7, 110.6, 110.6, 102.6, 102.5, 102.3, 50.0, 46.5, 30.0, 9.4.

Example 5: (R)-1-methyl-6-(2,3,5,6-tetrafluorophenyl)-2,5,6,7-tetrahydro-3H-pyrrolo[1,2-c]-imidazole-3-thione

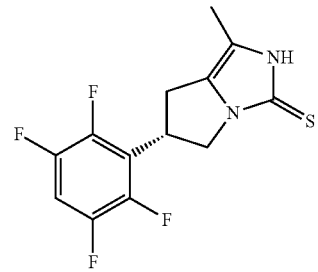

Compound was prepared in an analogous manner to Example 3 from (4R)-1-(tert-butoxycarbonyl)-4-(2,3,5,6-tetrafluorophenyl)pyrrolidine-2-carboxylic acid and methylmagnesium iodide and isolated as an off-white powder.
$^1$H NMR (DMSO-d6): 11.74 (1H, br s), 7.85 (1H, m), 4.49 (1H, quin, J=8.5 Hz), 4.42 (1H, m), 4.15 (1H, dd, J=11.6, 9.2 Hz), 3.76 (1H, dd, J=11.7, 7.8 Hz), 3.27 (1H, dd, J=15.6, 9.2 Hz), 2.89 (1H, dd, J=15.4, 7.9 Hz), 1.97 (3H, s).
$^{13}$C NMR (DMSO-d6): 155.0, 146.4, 146.3, 146.3, 145.3, 145.2, 144.8, 144.7, 144.6, 143.7, 143.6, 127.5, 120.5, 120.4, 120.3, 115.3, 105.9, 105.7, 105.6, 48.4, 35.9, 28.6, 9.3.

Example 6: (S)-1-methyl-6-(2,3,5,6-tetrafluorophenyl)-2,5,6,7-tetrahydro-3H-pyrrolo[1,2-c]imidazole-3-thione

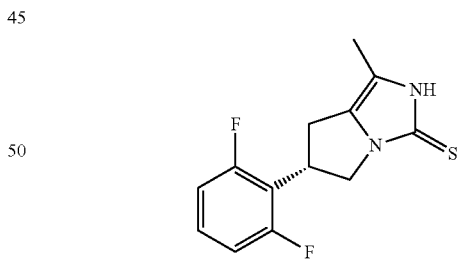

Compound was prepared in an analogous manner to Example 3 from (4S)-1-(tert-butoxycarbonyl)-4-(2,3,5,6-tetrafluorophenyl)pyrrolidine-2-carboxylic acid and methylmagnesium iodide and isolated as a light beige powder.
$^1$H NMR (DMSO-d6): 11.74 (1H, br s), 7.85 (1H, m), 4.49 (1H, quin, J=8.5 Hz), 4.15 (1H, dd, J=11.6, 9.2 Hz), 3.76 (1H, dd, J=11.7, 7.8 Hz), 3.27 (1H, dd, J=15.6, 9.2 Hz), 2.89 (1H, dd, J=15.4, 7.9 Hz), 1.97 (3H, s).
$^{13}$C NMR (DMSO-d6): 155, 146.4, 146.3, 146.3, 145.3, 145.2, 144.8, 144.7, 144.6, 143.7, 143.6, 127.5, 120.5, 120.4, 120.3, 115.3, 105.9, 105.7, 105.6, 48.7, 48.4, 35.9, 28.6, 9.3.

Example 7: (S)-6-(2,6-difluorophenyl)-1-methyl-2,5,6,7-tetrahydro-3H-pyrrolo[1,2-c]imidazole-3-thione

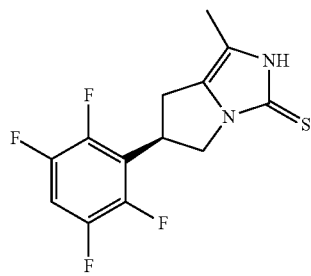 [SMILES: Cc1[nH]c(=S)n2c1C[C@H](c1c(F)c(F)cc(F)c1F)C2]

Compound was prepared in an analogous manner to Example 3 from (4S)-1-(tert-butoxycarbonyl)-4-(2,6-difluorophenyl)pyrrolidine-2-carboxylic acid and methylmagnesium iodide and isolated as a light beige powder.
$^1$H NMR (DMSO-d6): 11.72 (1H, br s), 7.40 (1H, m), 7.13 (2H, m), 4.41 (1H, quin, J=8.7 Hz), 4.12 (1H, br t, J=10.1 Hz), 3.70 (1H, dd, J=8.8, 10.8 Hz), 3.21 (1H, br dd, J=15.3, 9.2 Hz), 2.84 (1H, br dd, J=15.2, 8.6 Hz), 1.97 (3H, s).
$^{13}$C NMR (DMSO-d6): 161.6, 161.6, 160.0, 159.9, 155.0, 129.8, 129.7, 129.7, 127.8, 116.6, 116.5, 116.4, 115.2, 112.3, 112.2, 112.1, 112.1, 48.6, 35.4, 28.8, 9.3.

Example 8: (5aS,6aR)-5a-(5-chloro-2-fluorophenyl)-1-methyl-5,5a,6,6a-tetrahydrocyclopropa[3,4]pyrrolo[1,2-c]imidazole-3(2H)-thione

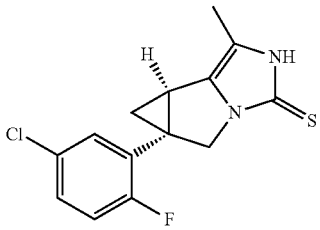 [SMILES: Cc1[nH]c(=S)n2c1[C@@H]1C[C@]1(c1cc(Cl)ccc1F)C2]

Compound was prepared in an analogous manner to Example 3 from tert-butyl (1S,5R)-1-(5-chloro-2-fluorophenyl)-4-(methoxy(methyl)carbamoyl)-3-azabicyclo[3.1.0]hexane-3-carboxylate and methylmagnesium iodide. The product was isolated as a beige solid.
$^1$H NMR (DMSO-d6): 11.65 (1H, br s), 7.47 (1H, dd, J=6.5, 2.6 Hz), 7.42 (1H, ddd, J=8.8, 4.4, 2.7 Hz), 7.29 (1H, dd, J=10.0, 8.9 Hz), 4.06 (1H, d, J=11.7 Hz), 3.77 (1H, d, J=12.0 Hz), 2.87 (1H, dd, J=8.2, 4.3 Hz), 2.04 (3H, m), 1.64 (1H, dd, J=8.1, 5.4 Hz), 1.12 (1H, t, J=4.8 Hz).
$^{13}$C NMR (DMSO-d6): 161.3, 159.7, 155.7, 130.3, 130.1, 130.1, 129.3, 129.3, 129.0, 128.9, 128.3, 128.3, 117.6, 117.4, 114.8, 51.5, 51.5, 32.3, 22.3, 20.2, 9.4.

Example 9: (5aS,6aR)-5a-(5-chloro-2-fluorophenyl)-1-(methyl-d$_3$)-5,5a,6,6a-tetrahydrocyclopropa[3,4]pyrrolo[1,2-c]imidazole-3(2H)-thione

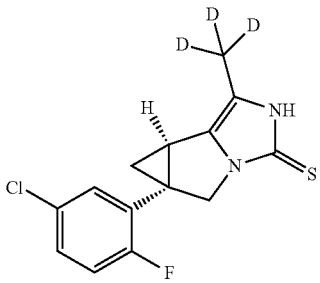 [SMILES: [2H]C([2H])([2H])c1[nH]c(=S)n2c1[C@@H]1C[C@]1(c1cc(Cl)ccc1F)C2]

Compound was prepared in an analogous manner to Example 3 from tert-butyl (1S,5R)-1-(5-chloro-2-fluorophenyl)-4-(methoxy(methyl)carbamoyl)-3-azabicyclo[3.1.0]hexane-3-carboxylate and methyl-d$_3$-magnesium iodide. The product was isolated as a light orange solid.
$^1$H NMR (DMSO-d6): 11.65 (1H, s), 7.47 (1H, dd, J=6.6, 2.8 Hz), 7.42 (1H, ddd, J=8.8, 4.4, 2.7 Hz), 7.29 (1H, m), 4.06 (1H, d, J=11.9 Hz), 3.77 (1H, d, J=12.0 Hz), 2.87 (1H, dd, J=8.3, 4.3 Hz), 1.64 (1H, dd, J=8.3, 5.4 Hz), 1.12 (1H, t, J=4.8 Hz).
$^{13}$C NMR (DMSO-d6): 161.3, 159.7, 155.7, 155.6, 130.3, 130.1, 130.1, 129.3, 129.3, 129.0, 128.9, 128.3, 128.3, 117.6, 117.4, 114.7, 114.6, 51.5, 51.5, 32.3, 22.3, 20.2.

Example 10: (R)-6-(3-chloro-2,6-difluorophenyl)-1-methyl-2,5,6,7-tetrahydro-3H-pyrrolo[1,2-c]imidazole-3-thione

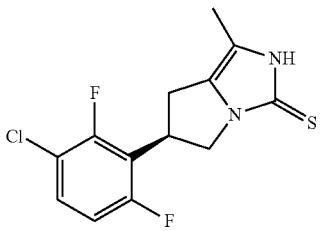 [SMILES: Cc1[nH]c(=S)n2c1C[C@H](c1c(F)ccc(Cl)c1F)C2]

Compound was prepared in an analogous manner to Example 3 from (4S)-1-(tert-butoxycarbonyl)-4-(3-chloro-2,6-difluorophenyl)pyrrolidine-2-carboxylic acid and methylmagnesium iodide and isolated as an off-white powder.
$^1$H NMR (DMSO-d6): 11.73 (1H, br s), 7.61 (1H, td, J=8.8, 5.6 Hz), 7.21 (1H, t, J=9.5 Hz), 4.44 (1H, quin, J=8.6 Hz), 4.13 (1H, dd, J=11.4, 9.2 Hz), 3.72 (1H, dd, J=11.6, 7.9 Hz), 3.23 (1H, m), 2.84 (1H, dd, J=15.5, 8.1 Hz), 1.97 (3H, s).
$^{13}$C NMR (DMSO-d6): 160.2, 160.1, 158.5, 158.5, 156.6, 156.5, 155, 154.9, 154.9, 129.7, 129.7, 127.7, 118.9, 118.7, 118.6, 116.1, 116.1, 116.0, 116.0, 115.2, 113.3, 113.3, 113.1, 113.1, 48.5, 35.8, 28.7, 9.4.

Example 11: (S)-6-(3-chloro-2,6-difluorophenyl)-1-methyl-2,5,6,7-tetrahydro-3H-pyrrolo[1,2-c]imidazole-3-thione

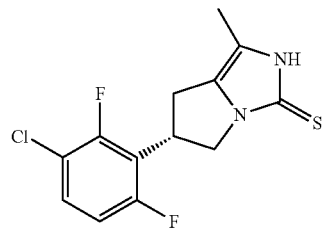 [SMILES: Cc1[nH]c(=S)n2c1C[C@@H](c1c(F)ccc(Cl)c1F)C2]

Compound was prepared in an analogous manner to Example 3 from (4R)-1-(tert-butoxycarbonyl)-4-(3-chloro-2,6-difluorophenyl)pyrrolidine-2-carboxylic acid and methylmagnesium iodide and isolated as a light beige powder.
$^1$H NMR (DMSO-d6): 11.73 (1H, br s), 7.61 (1H, td, J=8.8, 5.6 Hz), 7.21 (1H, t, J=9.5 Hz), 4.44 (1H, quin, J=8.6 Hz), 4.13 (1H, dd, J=11.4, 9.2 Hz), 3.72 (1H, dd, J=11.6, 7.9 Hz), 3.23 (1H, m), 2.84 (1H, dd, J=15.5, 8.1 Hz), 1.97 (3H, s).
$^{13}$C NMR (DMSO-d6): 160.2, 160.1, 158.5, 158.5, 156.6, 156.5, 154.9, 154.9, 129.7, 129.6, 127.7, 118.9, 118.7, 118.6, 116.1, 116.1, 116.0, 115.9, 115.2, 113.3, 113.3, 113.1, 113.1, 48.5, 35.7, 28.7, 9.4.

Example 12: (5aS,6aR)-5a-(3-bromo-2,6-difluorophenyl)-1-methyl-5,5a,6,6a-tetrahydrocyclopropa[3,4]pyrrolo[1,2-c]imidazole-3(2H)-thione

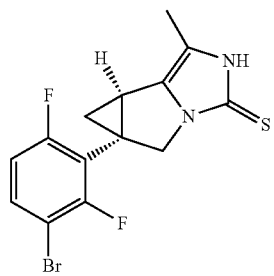 [SMILES: Cc1[nH]c(=S)n2c1[C@@H]1C[C@]1(c1c(F)ccc(Br)c1F)C2]

Compound was prepared in an analogous manner to Example 3 from 2-(5-bromo-2,6-difluorophenyl)acetonitrile and (R)-2-(chloromethyl)oxirane and isolated as a white solid.
$^1$H NMR (DMSO-d6): 11.68 (1H, br s), 7.74 (1H, td, J=8.4, 5.9 Hz), 7.15 (1H, td, J=9.2, 1.2 Hz), 4.01 (1H, d, J=12.3 Hz), 3.71 (1H, d, J=12.0 Hz), 2.72 (1H, dd, J=8.3, 4.5 Hz), 2.05 (3H, s), 1.65 (1H, dd, J=8.2, 5.6 Hz), 1.25 (1H, t, J=5.0 Hz).
$^{13}$C NMR(DMSO-d6): 161.9, 161.9, 160.3, 160.2, 158.8, 158.8, 157.2, 157.1, 155.7, 133.0, 133.0, 130.0, 117.2, 117.1, 115.1, 113.5, 113.3, 103.7, 103.7, 103.6, 51.4, 26.5, 21.8, 20.9, 9.4.

Example 13: (5aS,6aR)-5a-(5-bromo-2-fluorophenyl)-1-methyl-5,5a,6,6a-tetrahydrocyclopropa[3,4]pyrrolo[1,2-c]imidazole-3(2H)-thione

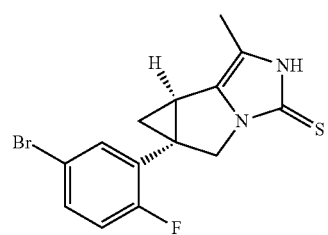

Step 1: ((1R,2S)-2-(aminomethyl)-2-(5-bromo-2-fluorophenyl)cyclopropyl)methanol

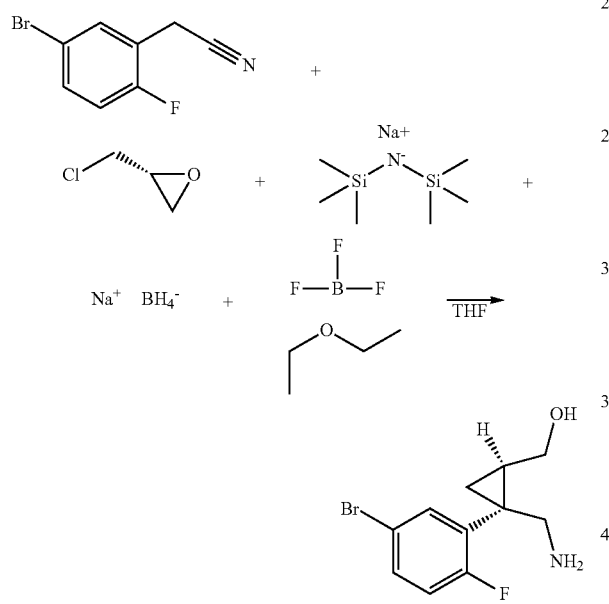

To a stirred solution of 2-(5-bromo-2-fluorophenyl)acetonitrile (10 g, 46.7 mmol) in dry tetrahydrofuran (100 mL), was added (R)-2-(chloromethyl)oxirane (4.38 mL, 56.1 mmol) at room temperature, under inert atmosphere. The reaction was then cooled to 0° C. and 2 M sodium bis(trimethylsilyl)amide in tetrahydrofuran (40.9 mL, 82 mmol) was added dropwise keeping the temperature between 0-5° C. Thereupon, the obtained red mixture was allowed to warm up to room temperature and stirred for 3 h. The reaction was diluted with dry tetrahydrofuran (100 mL), cooled to 0° C. and sodium borohydride (7.07 g, 187 mmol) was added, followed by dropwise addition of boron trifluoride diethyl etherate (23.68 mL, 187 mmol). The mixture was allowed to warm to room temperature naturally and stirred overnight. The obtained pale yellow suspension was then cooled to 0° C. and carefully quenched with 2 M HCl (140 ml, 280 mmol). The tetrahydrofuran was evaporated off under vacuum, the aqueous phase was washed with diethyl ether (discarded), then was basified to pH=10 (3 M NaOH) and extracted with dichloromethane. The organic phase was dried over MgSO₄, filtered and evaporated to leave a yellow oil. Yield: 11.75 g, 73%.

Step 2: tert-butyl (((1S,2R)-1-(5-bromo-2-fluorophenyl)-2-(hydroxymethyl)cyclopropyl)methyl)carbamate

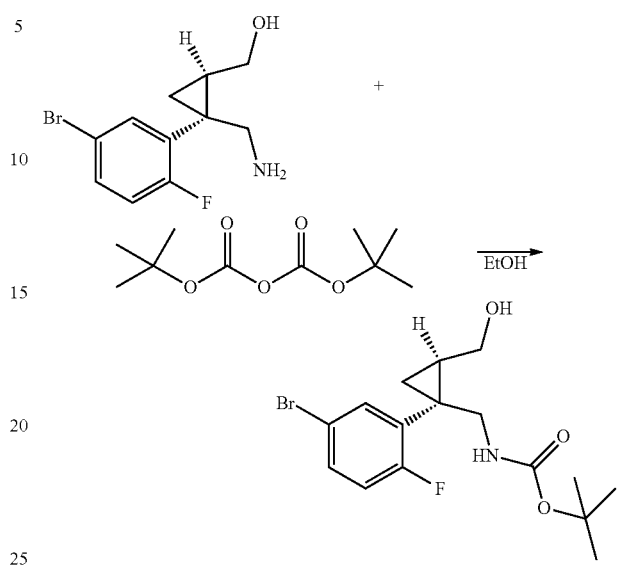

To an ice-cooled solution of ((1R,2S)-2-(aminomethyl)-2-(5-bromo-2-fluorophenyl)cyclopropyl)methanol (11.75 g, 42.9 mmol) in ethanol (145 mL), was added di-tert-butyl dicarbonate (9.35 g, 42.9 mmol). The solution was stirred at room temperature for 4 h. Then the solvent was evaporated and the residue was separated on a column. The titled compound was isolated as a yellow foam. Yield: 10.1 g, 56%.

Step 3: tert-butyl (1S,5R)-1-(5-bromo-2-fluorophenyl)-4-hydroxy-3-azabicyclo[3.1.0]hexane-3-carboxylate

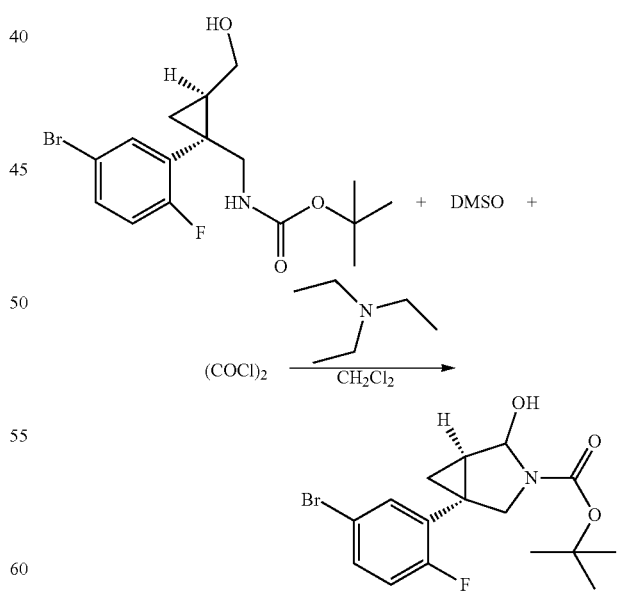

To a stirred solution of oxalyl dichloride (2.60 mL, 29.7 mmol) in dry dichloromethane (62.8 mL), was added dropwise a solution of DMSO (4.21 mL, 59.4 mmol) in dry dichloromethane (12.5 mL) at −78° C. over 30 min. The reaction mixture was stirred for 5 min in the cold, and then a solution of tert-butyl (((1S,2R)-1-(5-bromo-2-fluorophenyl)-2-(hydroxymethyl)cyclopropyl)methyl)carbamate (10.1 g, 27.0 mmol) in dry dichloromethane (25 mL) was added, dropwise over 30 min. The mixture was stirred at −78° C. for 1 h, and then triethylamine (18.8 mL, 135 mmol) was added. The reaction was allowed to warm up gradually to room temperature and stirred for 2 h. Thereupon the mixture was washed three times with water, dried over MgSO₄, filtered and evaporated to give a yellow oil. Yield: 10.1 g, 85%.

Step 4: tert-butyl (1S,5R)-1-(5-bromo-2-fluorophenyl)-4-cyano-3-azabicyclo[3.1.0]hexane-3-carboxylate

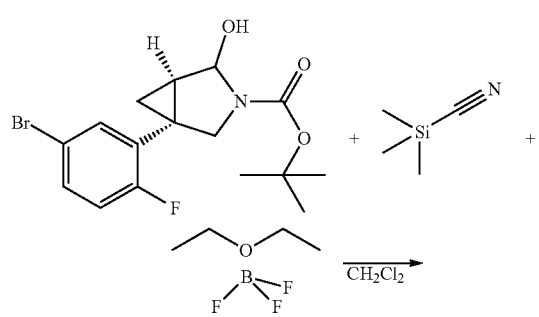

To a stirred solution of tert-butyl (1S,5R)-1-(5-bromo-2-fluorophenyl)-4-hydroxy-3-azabicyclo[3.1.0]hexane-3-carboxylate (10.1 g, 27.1 mmol) in dry dichloromethane (133 mL) was added trimethylsilanecarbonitrile (9.71 mL, 72.4 mmol) at room temperature under inert atmosphere. Then, the solution was cooled to −78° C. and boron trifluoride diethyl etherate (10.08 mL, 80.0 mmol) was added dropwise. The reaction mixture was stirred at −78° C. for 4 h., and then saturated solution of NaHCO₃ was added and the mixture was allowed to warm to room temperature. The organic phase was separated and aqueous phase was extracted with dichloromethane. The combined organic phases were dried over MgSO₄, filtered and evaporated to give 10.3 g of yellow oil. Yield: 85%.

Step 5: (1R,5S)-5-(5-bromo-2-fluorophenyl)-3-(tert-butoxycarbonyl)-3-azabicyclo[3.1.0]hexane-2-carboxylic acid

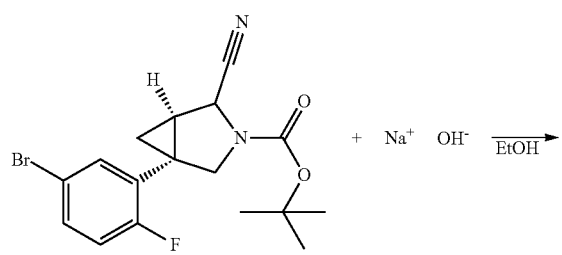

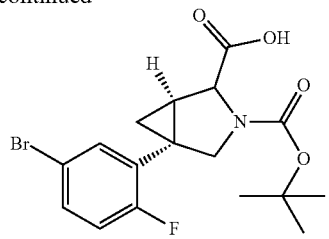

To a stirred solution of tert-butyl (1S,5R)-1-(5-bromo-2-fluorophenyl)-4-cyano-3-azabicyclo[3.1.0]hexane-3-carboxylate (10.3 g, 27.0 mmol) in ethanol (93 mL), at room temperature was added a solution of 3 M NaOH (45 mL, 135 mmol). The solution was heated at 80° C. for 3 h. Then, the reaction was cooled to room temperature, ethanol was evaporated and the aq. phase was acidified with 2N HCl solution, the resulting solid was filtered off, dissolved in a mixture of dichloromethane—isopropanol (7:3). The organic phase was dried over MgSO4, filtered and evaporated to give the titled product as a yellow semi-solid. Yield: 10.5 g, 78%.

Step 6: tert-butyl (1S,5R)-1-(5-bromo-2-fluorophenyl)-4-(methoxy(methyl)carbamoyl)-3-azabicyclo[3.1.0]hexane-3-carboxylate

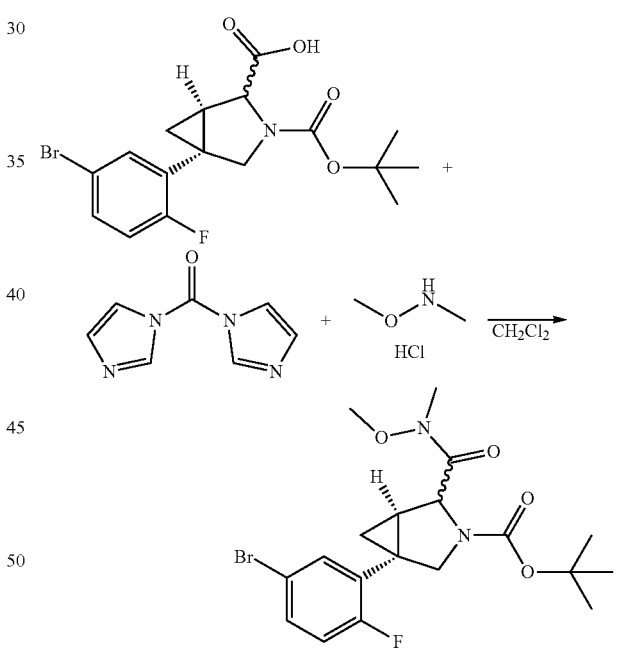

To a stirred solution of ((1R,5S)-5-(5-bromo-2-fluorophenyl)-3-(tert-butoxycarbonyl)-3-azabicyclo[3.1.0]hexane-2-carboxylic acid (2.5 g, 6.25 mmol) in anhydrous dichloromethane (36 mL) was added di(1H-imidazol-1-yl)methanone (1.215 g, 7.50 mmol) portion wise under nitrogen and the reaction stirred for 30 min. Thereupon, N,O-dimethylhydroxylamine hydrochloride (0.731 g, 7.50 mmol) was added and the mixture was stirred overnight. The reaction mixture was then diluted with dichloromethane (ca. to 60 mL) and washed with water. The organic phase was dried over MgSO4, filtered and evaporated to give the titled product as a yellow yellow oil. Yield: 1.57 g, 45%.

Step 7: tert-butyl (1S,5R)-4-acetyl-1-(5-bromo-2-fluorophenyl)-3-azabicyclo[3.1.0]hexane-3-carboxylate

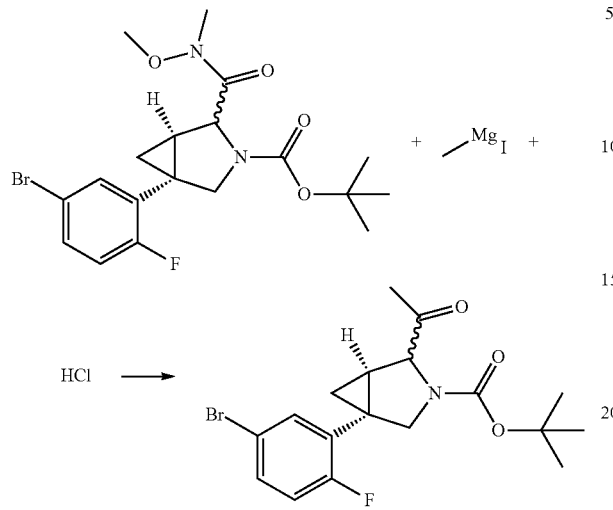

To a stirred solution of (1S,5R)-tert-butyl 1-(5-bromo-2-fluorophenyl)-4-(methoxy(methyl)carbamoyl)-3-azabicyclo[3.1.0]hexane-3-carboxylate (1.57 g, 3.54 mmol) in anhydrous tetrahydrofuran (15 mL) was added methylmagnesium iodide (3.54 ml, 10.62 mmol) dropwise at 0° C. The reaction mixture was stirred in the cold for 1 h, and then quenched by addition of 1 M HCl (14.17 ml, 14.17 mmol). The mixture was extracted with a mixture of ethyl acetate—petroleum ether (1:1). The organic phase was washed with brine, dried over MgSO₄, filtered and evaporated to give 1.34 g of yellow oil. Yield: 86%.

Step 8: 1-((1R,5S)-5-(5-bromo-2-fluorophenyl)-3-azabicyclo[3.1.0]hexan-2-yl)ethan-1-one hydrochloride

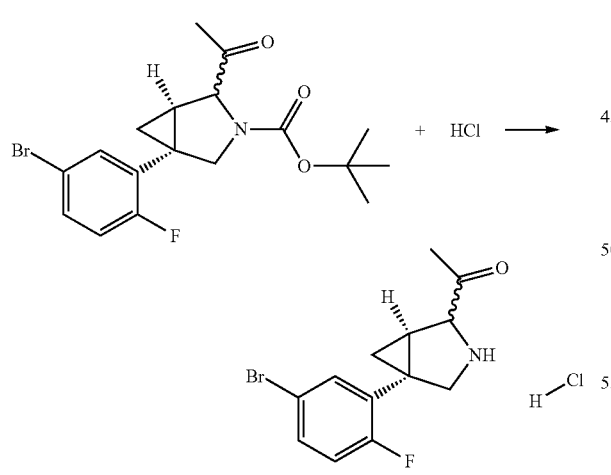

To a stirred solution of (1S,5R)-tert-butyl 4-acetyl-1-(5-bromo-2-fluorophenyl)-3-azabicyclo[3.1.0]hexane-3-carboxylate (1.33 g, 3.34 mmol) was added 4 M HCl in dioxane (6.68 mL, 26.7 mmol) and then the mixture was stirred at room temperature for 2 h. Thereupon, diethyl ether was added and the mixture was evaporated to dryness to give an orange oil. Yield: 1.2 g, 91%.

Step 9: (5aS,6aR)-5a-(5-bromo-2-fluorophenyl)-1-methyl-5,5a,6,6a-tetrahydrocyclopropa[3,4]pyrrolo[1,2-c]imidazole-3(2H)-thione

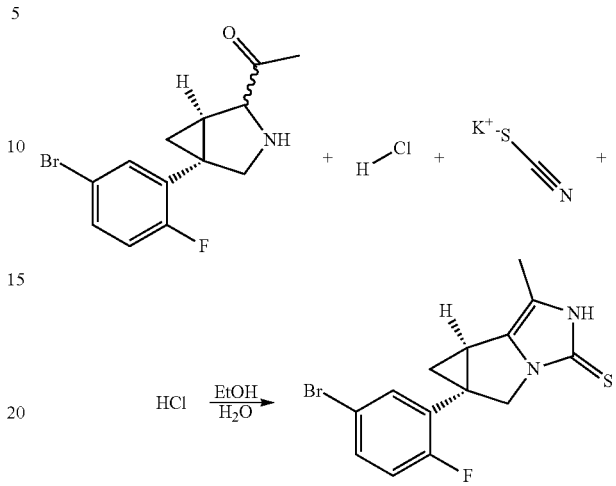

To a stirred solution of 1-((1R,5S)-5-(5-bromo-2-fluorophenyl)-3-azabicyclo[3.1.0]hexan-2-yl)ethanone hydrochloride (1.1 g, 3.29 mmol) in a mixture of ethanol (13.5 mL) and water (13.5 mL) was added potassium thiocyanate (0.351 g, 3.62 mmol) followed by addition of cc. HCl (0.135 mL, 1.644 mmol). The solution was heated at reflux for 1 h. The reaction was cooled to room temperature, and then ethanol was removed. The aqueous phase was extracted with dichloromethane, the organic phase was dried over MgSO₄, filtered and evaporated. Chromatography in a mixture of dichloromethane—methanol afforded the titled compound as a beige foam. Yield: 0.9 g, 77%.

¹H NMR (DMSO-d6): 11.65 (1H, s), 7.59 (1H, dd, J=6.7, 2.5 Hz), 7.55 (1H, ddd, J=8.7, 4.5, 2.6 Hz), 7.24 (1H, dd, J=10.1, 8.7 Hz), 4.05 (1H, d, J=12.0 Hz), 3.76 (1H, d, J=12.0 Hz), 2.87 (1H, dd, J=8.3, 4.3 Hz), 2.04 (3H, s), 1.64 (1H, dd, J=8.2, 5.3 Hz), 1.12 (1H, t, J=4.8 Hz).

¹³C NMR (DMSO-d6): 161.8, 160.2, 155.7, 132.9, 132.9, 132.3, 132.2, 130.2, 129.4, 129.3, 118, 117.8, 116.2, 116.2, 114.8, 51.5, 51.5, 32.2, 22.2, 20.2, 9.3.

Example 14: (5aS,6aR)-5a-(3-chloro-2,6-difluorophenyl)-1-methyl-5,5a,6,6a-tetrahydrocyclopropa[3,4]pyrrolo[1,2-c]imidazole-3(2H)-thione

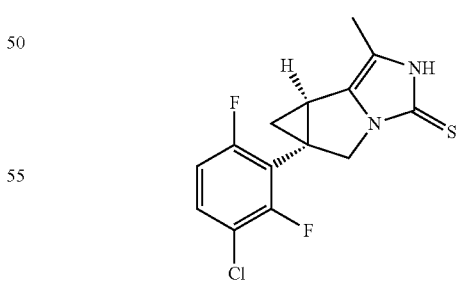

Compound was prepared in an analogous manner to Example 13 from 2-(3-chloro-2,6-difluorophenyl)acetonitrile. The product was isolated as a beige solid.

¹H NMR (DMSO-d6): 11.68 (1H, s), 7.63 (1H, td, J=8.6, 5.8 Hz), 7.21 (1H, t, J=8.6 Hz), 4.01 (1H, d, J=12.2 Hz), 3.72 (1H, d, J=12.2 Hz), 2.73 (1H, dd, J=8.2, 4.4 Hz), 2.05 (3H, s), 1.65 (1H, dd, J=8.2, 5.6 Hz), 1.25 (1H, t, J=5.0 Hz).

$^{13}$C NMR (DMSO-d6): 161.2, 161.2, 159.6, 159.6, 157.8, 157.8, 156.2, 156.1, 155.7, 130.3, 130.2, 129.9, 117.2, 117.1, 117, 115.7, 115.7, 115.6, 115.6, 115.1, 112.9, 112.9, 112.8, 112.8, 51.4, 26.4, 21.7, 20.8, 9.4.

Example 15: (R)-6-(3-bromo-2,6-difluorophenyl)-1-methyl-2,5,6,7-tetrahydro-3H-pyrrolo[1,2-c]imidazole-3-thione

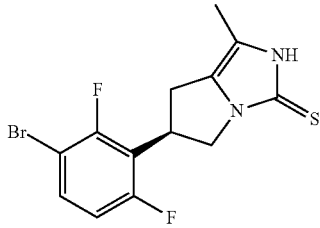

Compound was prepared in an analogous manner to Example 20 from 3-bromo-2,6-difluorobenzaldehyde and isolated as a beige powder.

$^1$H NMR (DMSO-d6): 11.73 (1H, br s), 7.72 (1H, ddd, J=8.9, 8.1, 5.8 Hz), 7.16 (1H, m), 4.44 (1H, quin, J=8.6 Hz), 4.13 (1H, dd, J=11.5, 9.2 Hz), 3.71 (1H, dd, J=11.6, 7.9 Hz), 3.23 (1H, dd, J=15.5, 9.3 Hz), 2.84 (1H, dd, J=15.4, 8.1 Hz), 1.97 (3H, s).

$^{13}$C NMR (DMSO-d6): 160.8, 160.8, 159.2, 159.1, 157.5, 157.5, 155.9, 155.8, 155, 132.4, 132.4, 127.7, 118.8, 118.7, 118.6, 115.1, 113.8, 113.8, 113.6, 113.6, 104.1, 104, 103.9, 103.9, 48.5, 35.8, 28.7, 9.3.

Example 16: (S)-6-(3-bromo-2,6-difluorophenyl)-1-methyl-2,5,6,7-tetrahydro-3H-pyrrolo[1,2-c]imidazole-3-thione

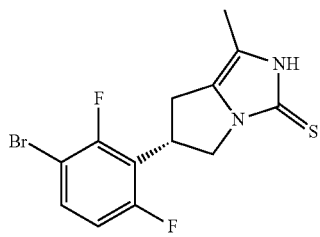 [SMILES: Cc1[nH]c(=S)n2c1C[C@@H](c1c(F)ccc(Br)c1F)C2]

Compound was prepared in an analogous manner to Example 20 from 3-bromo-2,6-difluorobenzaldehyde using 4-((R)-hydroxy((1S,2S,4S,5R)-5-vinylquinuclidin-2-yl)methyl)quinolin-6-ol as catalyst (CAS #524-63-0) and isolated as a beige powder.

$^1$H NMR (DMSO-d6): 11.72 (1H, br s), 7.72 (1H, ddd, J=8.9, 8.1, 5.8 Hz), 7.16 (1H, m), 4.44 (1H, t, J=8.7 Hz), 4.13 (1H, dd, J=11.5, 9.2 Hz), 3.71 (1H, dd, J=11.6, 7.9 Hz), 3.23 (1H, dd, J=15.5, 9.3 Hz), 2.84 (1H, dd, J=15.5, 8.1 Hz), 1.97 (3H, s).

$^{13}$C NMR (DMSO-d6): 160.8, 160.8, 159.2, 159.1, 157.5, 157.5, 155.9, 155.8, 155, 132.4, 132.4, 127.7, 118.8, 118.7, 118.6, 115.1, 113.8, 113.8, 113.6, 113.6, 104.1, 104, 103.9, 103.9, 48.5, 35.8, 28.7, 9.3.

Example 17: (5aS,6aR)-5a-(3-chloro-5-fluorophenyl)-1-methyl-5,5a,6,6a-tetrahydrocyclopropa[3,4]pyrrolo[1,2-c]imidazole-3(2H)-thione

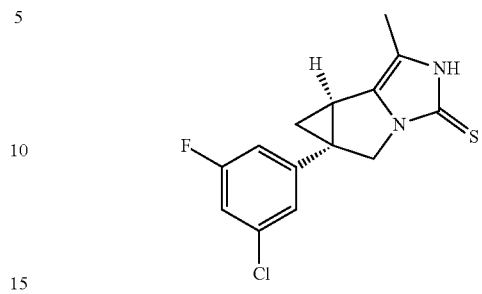

Compound was prepared in an analogous manner to Example 13 from 2-(3-chloro-5-fluorophenyl)acetonitrile. The product was isolated as a beige solid.

$^1$H NMR (DMSO-d6): 11.64 (1H, s), 7.30 (1H, dt, J=8.7, 2.1 Hz), 7.28 (1H, t, J=1.6 Hz), 7.23 (1H, dt, J=10.0, 1.8 Hz), 4.19 (1H, d, J=12.2 Hz), 3.99 (1H, d, J=12.0 Hz), 3.00 (1H, dd, J=8.3, 4.3 Hz), 2.03 (3H, s), 1.64 (1H, dd, J=8.3, 5.2 Hz), 1.14 (1H, t, J=4.8 Hz).

$^{13}$C NMR (DMSO-d6): 163.1, 161.4, 156, 145, 144.9, 134.1, 134.1, 130.2, 123, 123, 114.5, 114.3, 114.1, 112.9, 112.8, 50.8, 36, 36, 25.2, 22.2, 9.3.

Example 18: (5aS,6aR)-5a-(5-bromo-2-fluorophenyl)-1-(methyl-d$_3$)-5,5a,6,6a-tetrahydrocyclopropa[3,4]pyrrolo[1,2-c]imidazole-3(2H)-thione

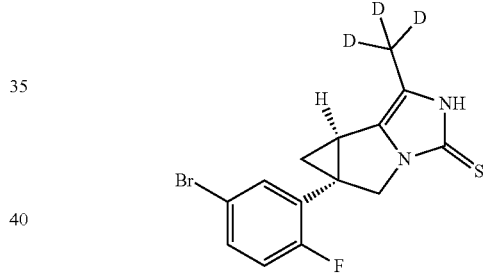

Compound was prepared in an analogous manner to Example 13 from 2-(5-bromo-2-fluorophenyl)acetonitrile. The product was isolated as a beige solid.

$^1$H NMR (DMSO-d6): 11.65 (1H, s), 7.59 (1H, dd, J=6.7, 2.6 Hz), 7.55 (1H, ddd, J=8.7, 4.5, 2.6 Hz), 7.23 (1H, dd, J=10.1, 8.7 Hz), 4.05 (1H, d, J=12.0 Hz), 3.76 (1H, d, J=12.0 Hz), 2.87 (1H, dd, J=8.2, 4.3 Hz), 1.64 (1H, dd, J=8.3, 5.4 Hz), 1.12 (1H, t, J=4.8 Hz).

$^{13}$C NMR (DMSO-d6): 161.8, 160.2, 155.7, 132.9, 132.9, 132.3, 132.2, 130.3, 129.4, 129.3, 118, 117.8, 116.2, 116.2, 114.7, 51.5, 51.5, 32.3, 22.2, 20.2.

Example 19: (S)-6-(5-bromo-2-fluorophenyl)-1-methyl-2,5,6,7-tetrahydro-3H-pyrrolo[1,2-c]imidazole-3-thione

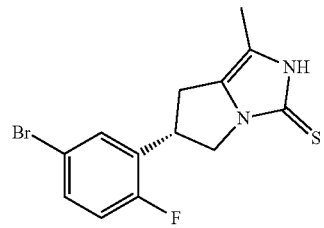

Compound was prepared in an analogous manner to Example 20 from 5-bromo-2-fluorobenzaldehyde using 4-((R)-hydroxy((1S,2S,4S,5R)-5-vinylquinuclidin-2-yl)methyl)quinolin-6-ol as catalyst (CAS #524-63-0) and isolated as an off-white solid.

$^1$H NMR(DMSO-d6): 11.70 (1H, br s), 7.58 (1H, dd, J=6.7, 2.5 Hz), 7.53 (1H, ddd, J=8.7, 4.5, 2.5 Hz), 7.23 (1H, dd, J=10.3, 8.8 Hz), 4.20 (1H, quin, J=8.1 Hz), 4.11 (1H, dd, J=10.9, 8.1 Hz), 3.71 (1H, dd, J=11.3, 7.9 Hz), 3.18 (1H, dd, J=15.2, 8.1 Hz), 2.85 (1H, ddd, J=15.2, 8.3, 1.2 Hz), 1.98 (3H, s).

$^{13}$C NMR(DMSO-d6): 160.3, 158.7, 155.1, 131.8, 131.8, 131.4, 131.4, 130.6, 130.5, 127.5, 118, 117.9, 116.5, 116.4, 115.4, 49, 40.5, 29, 9.3.

Example 20: (R)-1-methyl-6-(2,3,6-trifluorophenyl)-6,7-dihydro-2H-pyrrolo[1,2-c]imidazole-3(5H)-thione

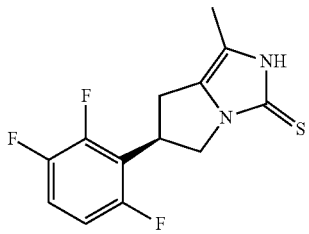 [SMILES: Cc1[nH]c(=S)n2c1C[C@H](c1c(F)ccc(F)c1F)C2]

To a solution of methanol (90 mL) and 1.5 M sodium hydroxide (131 mL, 197 mmol) was added a solution of 2,3,6-trifluorobenzaldehyde (30 g, 187 mmol) and nitromethane (16 mL, 299 mmol) in methanol (60 mL) dropwise over 40 min at 5° C., while the internal temperature was maintained between 5 and 10° C. with external cooling. The reaction was then agitated in the cold for 30 min., and then a solution of acetic acid (16 mL, 281 mmol) was added in one portion at 0-10° C. with stirring. The resulting mixture extracted with dichloromethane (ca. 200 mL), the organic phase was washed with brine, dried (MgSO$_4$), filtered to give 1-(3-bromo-2,6-difluorophenyl)-2-nitroethanol solution in dichloromethane. Thereupon, the above solution (ca. 270 mL) was treated with N,N-dimethylpyridin-4-amine (2.289 g, 18.74 mmol) followed by addition of acetic anhydride (21.26 ml, 225 mmol) and the mixture was stirred at room temperature overnight. The reaction mixture was then washed with water and sodium bicarbonate solution, respectively. The organic phase was dried over MgSO$_4$, filtered and evaporated to dryness. The crude product was crystallized from a mixture of isopropanol and water to give a light brownish solid. Yield: 38.1 g, 88%.

Step 2: diethyl (R)-2-(2-nitro-1-(2,3,6-trifluorophenyl)ethyl)malonate

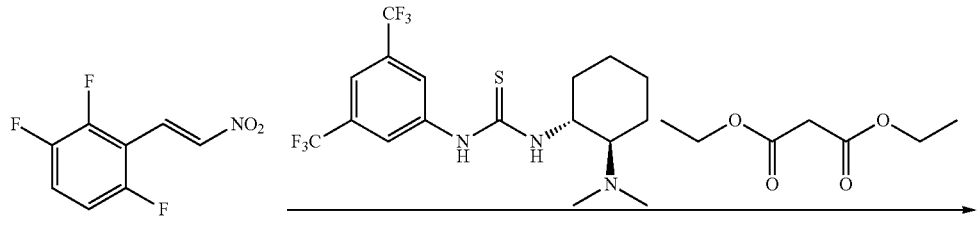

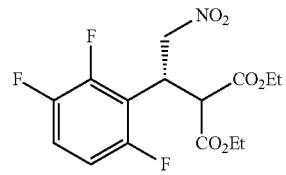

Step 1: (E)-1,2,4-trifluoro-3-(2-nitrovinyl)benzene

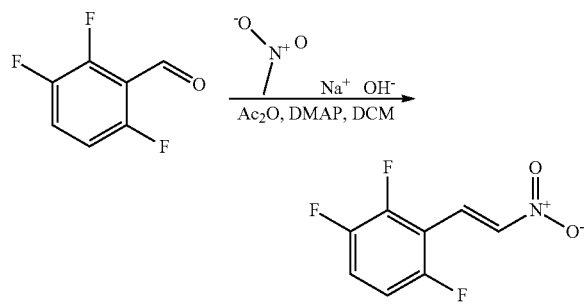

To a cold solution of (E)-1,2,4-trifluoro-3-(2-nitrovinyl)benzene (5 g, 24.62 mmol) and 1-(3,5-bis(trifluoromethyl)phenyl)-3-((1R,2R)-2-(dimethylamino)cyclohexyl)thiourea (CAS #620960-26-1) (0.305 g, 0.738 mmol) in dry toluene (40 ml) was added diethyl malonate (4.88 mL, 32.0 mmol) and the solution was kept for 16 h at −20° C. (in the freezer), the reaction was then warmed up to room temperature, washed with 30 mL of 1 M HCl solution, dried over MgSO$_4$, filtered through a silica pad and evaporated to dryness to give (R)-diethyl 2-(2-nitro-1-(2,3,6-trifluorophenyl)ethyl)malonate as a yellowish oil. Yield: 10.3 g, 98%.

Step 3: ethyl (4R)-2-oxo-4-(2,3,5-trifluorophenyl)pyrrolidine-3-carboxylate

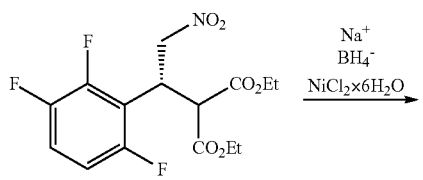 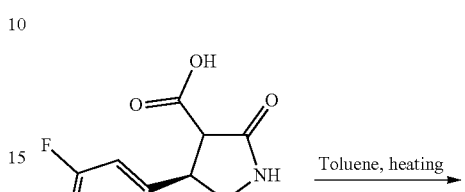

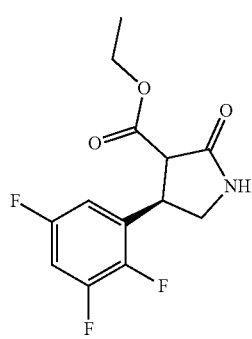

To a suspension of (R)-diethyl 2-(2-nitro-1-(2,3,6-trifluorophenyl)ethyl)malonate (10.3 g, 22.68 mmol) in methanol (115 mL) was added nickel(II) chloride hexahydrate (5.39 g, 22.68 mmol) followed by addition of sodium borohydride (6.86 g, 181 mmol) in portions with ice cooling over 30 min. The mixture was stirred for 5 h at room temperature, then quenched with 2 M HCl solution (60 mL) followed by addition of cc. ammonia (5 mL). The mixture was then diluted with dichloromethane (150 mL), acidified with 6 M HCl to pH=2, and stirred for 16 h to give a clear solution. Thereupon, the mixture was extracted with dichloromethane, the organic phase was dried over MgSO$_4$, filtered and evaporated to dryness. Crystallization from petroleum ether gave the titled product as a light beige powder. (Yield: 6.19 g, 95%).

Step 4: (4R)-2-oxo-4-(2,3,5-trifluorophenyl)pyrrolidine-3-carboxylic acid

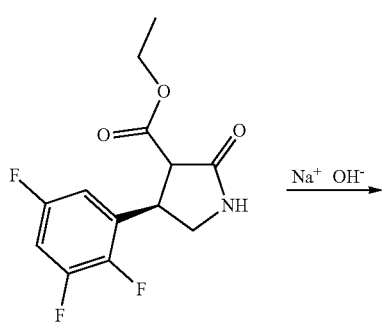

To a stirred solution (4R)-ethyl 2-oxo-4-(2,3,6-trifluorophenyl)pyrrolidine-3-carboxylate (6 g, 20.89 mmol) in ethanol (90 mL) was added 1 M sodium hydroxide (25.1 mL, 25.1 mmol). The resulting suspension was stirred for 2 h at room temperature, the organics were then removed under vacuum, and the residue was dissolved in water (50 mL). The product was crystallized on acidification with 6 M HCl. The resulting crystals were collected, washed with cold water and dried under vacuum at 50° C. to give the product as a beige powder. Yield: 4.75 g, 88%.

Step 5: (R)-4-(2,3,5-trifluorophenyl)pyrrolidin-2-one

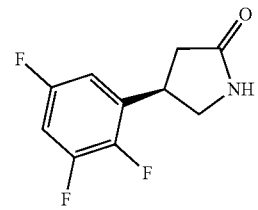

A solution of (4R)-2-oxo-4-(2,3,6-trifluorophenyl)pyrrolidine-3-carboxylic acid (4.64 g, 17.90 mmol) in toluene (150 mL) was stirred under reflux for 3 h, thereupon, the mixture was evaporated to 30 mL followed by addition of petroleum ether afforded the titled product as a beige powder. Yield: 3.45 g, 90%.

Step 6: tert-butyl (R)-2-oxo-4-(2,3,5-trifluorophenyl)pyrrolidine-1-carboxylate

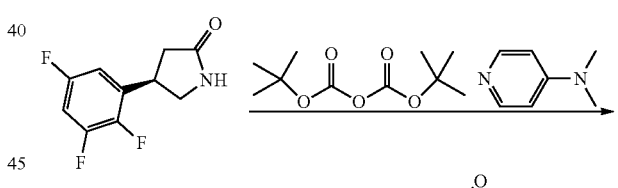

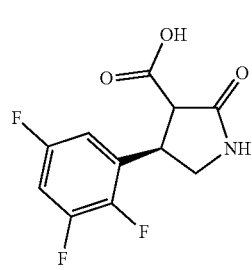

To a stirred solution of (R)-4-(2,3,6-trifluorophenyl)pyrrolidin-2-one (3.35 g, 15.57 mmol)) in dry dichloromethane (14 mL) was added at room temperature di-tert-butyl dicarbonate (5.10 g, 23.35 mmol) followed by addition of N,N-dimethylpyridin-4-amine (1.902 g, 15.57 mmol). The mixture was then stirred at room temperature for 24 h at room temperature, and then diluted with dichloromethane to 80 mL washed with 10% citric acid (80 mL). The organic phase was dried (MgSO$_4$), filtered through silica pad, and then the filtrate was evaporated to dryness. Crystallization from petroleum ether afforded (R)-tert-butyl 2-oxo-4-(2,3,6-trifluorophenyl)pyrrolidine-1-carboxylate as an off-white powder. Yield: 4.15 g, 85%.

Step 7: tert-butyl (4R)-2-hydroxy-4-(2,3,5-trifluorophenyl)pyrrolidine-1-carboxylate

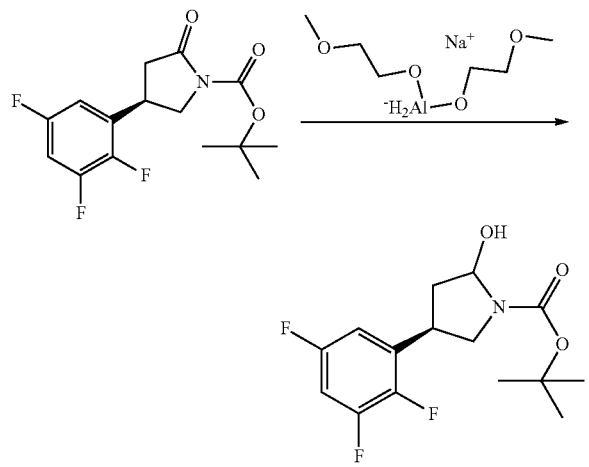

To a stirred solution of (R)-tert-butyl 2-oxo-4-(2,3,6-trifluorophenyl)pyrrolidine-1-carboxylate (4 g, 12.69 mmol) in a mixture of dry diethyl ether (39 mL) and tetrahydrofuran (13 mL) was added dropwise 65% RED-Al (bis(2-methoxyethoxy)aluminum(III) sodium hydride) (2.67 mL, 8.88 mmol) in toluene at 5-7° C. under nitrogen and the mixture was stirred for 1 h in the cold. Thereupon, the mixture was quenched with sodium bicarbonate solution (ca. 40 mL) and stirred for 30 min. The organic phase was dried over MgSO₄, filtered and evaporated to dryness to give the product as a yellowish oil. (Yield: 4.55 g, 96%).

Step 8: tert-butyl (4R)-2-cyano-4-(2,3,5-trifluorophenyl)pyrrolidine-1-carboxylate

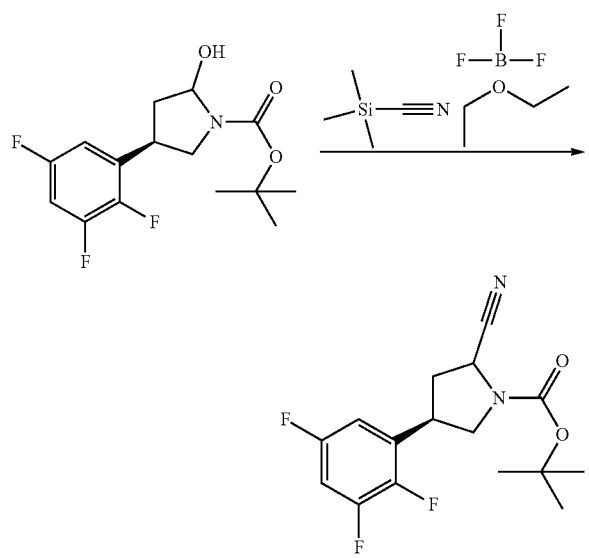

To a stirred solution of (4R)-tert-butyl 2-methoxy-4-(2,3,6-trifluorophenyl)pyrrolidine-1-carboxylate (4.33 g, 11.76 mmol) in dry dichloromethane (90 mL) was added trimethylsilanecarbonitrile (3.15 mL, 23.52 mmol) followed by addition of boron trifluoride diethyl etherate (3.28 mL, 25.9 mmol) at -70° C. The mixture was stirred for 4 h in the cold, quenched with sodium bicarbonate solution, and then allowed to warm up with stirring to room temperature. The organic phase was dried over MgSO₄, filtered and evaporated to dryness under vacuum to give the titled compound as a yellowish oil. (Yield: 4.41 g, 98%).

Step 9: tert-butyl (4R)-2-carbamoyl-4-(2,3,6-trifluorophenyl)pyrrolidine-1-carboxylate

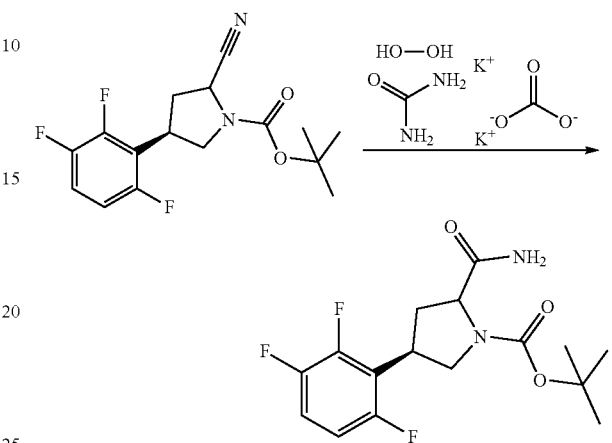

To a stirred solution of (4R)-tert-butyl 2-cyano-4-(2,3,6-trifluorophenyl)pyrrolidine-1-carboxylate (4.4 g, 11.46 mmol) in a mixture of acetone (54 mL) and water (18 mL) was added urea hydrogen peroxide complex (5.39 g, 57.3 mmol) followed by potassium carbonate (0.317 g, 2.292 mmol) and the reaction was stirred at room temperature for 16 h. Acetone was then partially removed under vacuum until oil separation. The mixture was diluted with water and petroleum ether, aged with stirring for 1 h at 5-7° C. (crystallization occurred). The solid was collected, washed with water, petroleum ether and dried to give (4R)-tert-butyl 2-carbamoyl-4-(2,3,6-trifluorophenyl)pyrrolidine-1-carboxylate. Yield: 3.46 g, 88%.

Step 10: (4R)-1-(tert-butoxycarbonyl)-4-(2,3,6-trifluorophenyl)pyrrolidine-2-carboxylic acid

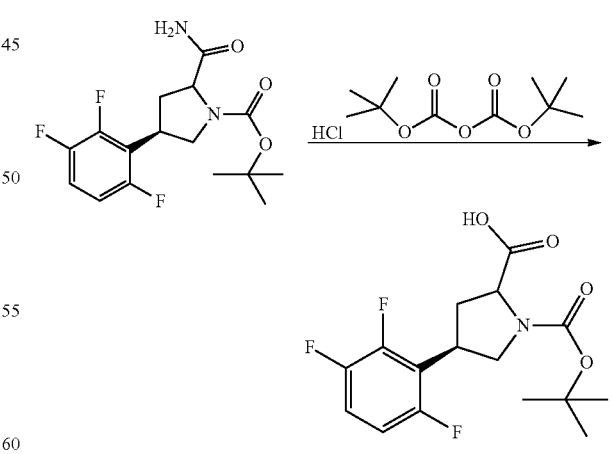

A stirred suspension of (4R)-tert-butyl 2-carbamoyl-4-(2,3,6-trifluorophenyl)pyrrolidine-1-carboxylate (3.36 g, 9.76 mmol) in 2 M HCl (73 mL, 146 mmol) was refluxed for 3 h to give a clear solution with minimum amount of dark insoluble material. After being cooled to room temperature the solid was filtered off and the filtrate was concentrated under vacuum. The residue was dissolved in water (ca. 50 mL), the pH was adjusted to 7 by addition of 1 M NaOH (19.52 mL, 19.52 mmol). The solution was then concentrated to approx. 50 mL and methanol (55 mL) was added followed by addition of di-tert-butyl dicarbonate (2.343 g, 10.73 mmol) and the mixture was stirred for 45 min. Methanol was then removed under vacuum, the residue was diluted with water (25 mL) and washed with petroleum ether. The aqueous phase was acidified to pH=1-2 by addition of 2 M HCl, and then extracted with DCM (50 ml). The organic phase was dried over MgSO$_4$, filtered and evaporated to dryness to give (4R)-1-(tert-butoxycarbonyl)-4-(2,3,6-trifluorophenyl)pyrrolidine-2-carboxylic acid as a light beige powder. Yield: 2.8 g, 83%.

Step 11-14: (R)-1-methyl-6-(2,3,6-trifluorophenyl)-2,5,6,7-tetrahydro-3H-pyrrolo[1,2-c]imidazole-3-thione

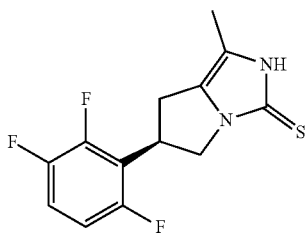 [SMILES: Cc1[nH]c(=S)n2c1C[C@H](c1c(F)ccc(F)c1F)C2]

Compound was prepared in an analogous manner to Example 13 (Steps 6-9) from (4R)-1-(tert-butoxycarbonyl)-4-(2,3,6-trifluorophenyl)pyrrolidine-2-carboxylic acid and isolated as an off-white powder.

$^1$H NMR (DMSO-d6): 11.72 (1H, br s), 7.47 (1H, qd, J=9.4, 5.0 Hz), 7.17 (1H, tdd, J=9.6, 9.6, 3.7, 1.9 Hz), 4.43 (1H, quin, J=8.7 Hz), 4.14 (1H, dd, J=11.3, 9.2 Hz), 3.73 (1H, dd, J=11.5, 8.1 Hz), 3.24 (1H, dd, J=15.6, 9.2 Hz), 2.86 (1H, dd, J=15.4, 8.4 Hz), 1.97 (3H, s).

$^{13}$C NMR (DMSO-d6): 156.9, 156.9, 156.9, 156.9, 155.3, 155.3, 155.3, 155.3, 155, 149.1, 149, 149, 148.9, 147.5, 147.5, 147.4, 147.4, 147.3, 147.3, 145.9, 145.9, 145.8, 145.8, 127.6, 118.9, 118.8, 118.8, 118.7, 116.5, 116.4, 116.3, 116.3, 115.2, 112, 112, 111.9, 111.9, 111.8, 111.8, 111.8, 111.7, 48.4, 35.7, 28.6, 9.3.

Example 21: (R)-6-(5-bromo-2-fluorophenyl)-1-methyl-2,5,6,7-tetrahydro-3H-pyrrolo[1,2-c]imidazole-3-thione

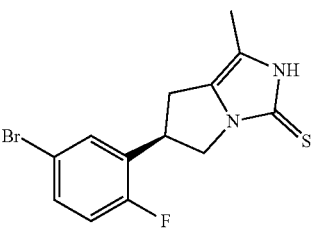 [SMILES: Cc1[nH]c(=S)n2c1C[C@H](c1cc(Br)ccc1F)C2]

Compound was prepared in an analogous manner to Example 20 from 5-bromo-2-fluorobenzaldehyde and isolated as an off-white solid.

$^1$H NMR (DMSO-d6): 11.70 (1H, br s), 7.58 (1H, dd, J=6.6, 2.5 Hz), 7.53 (1H, ddd, J=8.7, 4.5, 2.5 Hz), 7.23 (1H, dd, J=10.3, 8.7 Hz), 4.20 (1H, quin, J=8.1 Hz), 4.11 (1H, dd, J=10.9, 8.2 Hz), 3.71 (1H, dd, J=11.3, 7.9 Hz), 3.18 (1H, dd, J=15.2, 8.1 Hz), 2.85 (1H, ddd, J=15.2, 8.4, 1.1 Hz), 1.98 (3H, s).

$^{13}$C NMR (DMSO-d6): 160.3, 158.7, 155.1, 131.8, 131.8, 131.4, 131.4, 130.6, 130.5, 127.6, 118, 117.9, 116.5, 116.4, 115.4, 49, 40.5, 29, 9.3.

Example 22: (R)-6-(2,6-difluorophenyl)-1-methyl-2,5,6,7-tetrahydro-3H-pyrrolo[1,2-c]imidazole-3-thione

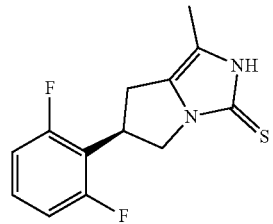 [SMILES: Cc1[nH]c(=S)n2c1C[C@H](c1c(F)cccc1F)C2]

Compound was prepared in an analogous manner to Example 20 from 2,6-difluorobenzaldehyde and isolated as an off-white solid.

$^1$H NMR (DMSO-d6): 11.72 (1H, br s), 7.40 (1H, tt, J=8.4, 6.6 Hz), 7.13 (2H, m), 4.41 (1H, quin, J=8.8 Hz), 4.12 (1H, m), 3.70 (1H, dd, J=11.4, 8.4 Hz), 3.21 (1H, dd, J=15.2, 9.2 Hz), 2.84 (1H, dd, J=15.4, 8.7 Hz), 1.97 (3H, s).

$^{13}$C NMR (DMSO-d6): 161.6, 161.6, 160, 159.9, 155, 129.8, 129.7, 129.7, 127.8, 116.6, 116.5, 116.4, 115.2, 112.3, 112.2, 112.1, 112.1, 48.6, 35.4, 28.8, 9.3.

Example 23: (S)-6-(5-chloro-2-fluorophenyl)-1-methyl-2,5,6,7-tetrahydro-3H-pyrrolo[1,2-c]imidazole-3-thione

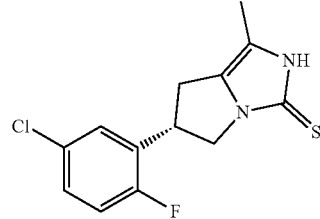 [SMILES: Cc1[nH]c(=S)n2c1C[C@@H](c1cc(Cl)ccc1F)C2]

Compound was prepared in an analogous manner to Example 20 from 5-chloro-2-fluorobenzaldehyde using 4-((R)-hydroxy((1S,2S,4S,5R)-5-vinylquinuclidin-2-yl)methyl)quinolin-6-ol as catalyst (CAS #524-63-0) and isolated as a beige solid.

$^1$H NMR (DMSO-d6): 11.70 (1H, br s), 7.46 (1H, dd, J=6.5, 2.7 Hz), 7.40 (1H, ddd, J=8.8, 4.4, 2.6 Hz), 7.29 (1H, dd, J=10.1, 8.8 Hz), 4.20 (1H, quin, J=8.1 Hz), 4.11 (1H, dd, J=10.8, 8.1 Hz), 3.72 (1H, dd, J=11.3, 7.9 Hz), 3.18 (1H, dd, J=15.1, 8.1 Hz), 2.85 (1H, ddd, J=15.2, 8.3, 1.2 Hz), 1.98 (3H, s).

$^{13}$C NMR (DMSO-d6): 159.8, 158.2, 155.1, 130.2, 130.1, 128.9, 128.8, 128.5, 128.5, 127.6, 117.6, 117.4, 115.5, 49.1, 49.1, 40.5, 29, 9.3.

G. Dopamine-β-Hydroxylase Inhibition Assays

The ability of a compound to inhibit DβH activity may be assessed using the following cell assay. For the purposes of the present invention, a compound is considered to be a "DβH inhibitor" if it exhibits activity in "% of control" of ≤20% at 10 μm in this cell assay. Preferred compounds of the present invention (including most of the specific Examples above) exhibit activity in "% of control" of ≤50% at 1.0 μm in this cell assay. More preferred compounds of the present invention exhibit activity in "% of control" of ≤20% at 1.0 µm in this cell assay. Especially preferred compounds of the present invention exhibit activity in "% of control" of ≤50% at 100 nm in this assay.

SK—N—SH cells (ATCC HTB-11), obtained from LGC Standards (Teddington, UK) were cultured in Eagle's minimum essential medium supplemented with 25 mM Hepes, 100 U/mL penicillin G, 0.25 µg/mL amphotericin B, 100 µg/mL streptomycin and 10% Gibco® fetal bovine serum. Cells were grown in T162 cm flasks (Corning, N.Y.) in a humidified atmosphere of 5% $CO_2$-95% air at 37° C. Fetal bovine serum was removed from cells for 4 h prior to collection.

For the preparation of cellular homogenates, media was removed and cell monolayers were washed with 50 mM Tris-HCl pH 7.4. Cells were subsequently scrapped off the flasks and were resuspended in 50 mM Tris pH 7.4. Cell suspensions were homogenized with SilentCrusher M (Heidolph) for a short stroke and resultant homogenates were aliquoted and stored frozen at −80° C.

Total protein was quantified in cellular homogenates with BioRad Protein Assay (BioRad) using a standard curve of BSA (50-250 µg/mL).

DβH activity was measured by a modification of the method of Nagatsu and Udenfriend (Nagatsu, T. and S. Udenfriend: "Photometric assay of dopamine-hydroxylase activity in human blood." *Clin. Chem.* 18(9): 980-3, 1972) which is based on the enzymatic hydroxylation of tyramine into octopamine. The octopamine formed is subsequently oxidized to p-hydroxybenzaldehyde and measured by spectrophotometry. In brief, reaction mixture (total volume 500 µl) contained: cellular homogenate (75 µg total protein) sodium acetate pH 5.0 (200 mM), NEM (30 mM), $CuSO_4$ (5 µM), catalase aqueous solution (0.5 mg/mL), pargyline-HCl (1 mM), sodium fumarate (10 mM), ascorbic acid (10 mM), inhibitor or vehicle and tyramine (25 mM). After a 10 min pre-incubation period at 37° C., the reaction was initiated by the addition of tyramine. Reaction was carried out for 45 min at 37° C. before termination with 50 µl PCA (2 M). Samples were centrifuged for 3 min at 16100 g and supernatants were subjected to solid phase extraction. Solid phase extraction was performed using either SPE cartridges ISO-LUTE SCX-3 (100 mg, 1 mL) or SPE 2 mL fixed 96 well plates ISOLUTE SCX-3 (100 mg) previously equilibrated with MilliQ water. Columns/plates were centrifuged at 150 g for 2 min. Eluate was discarded and matrix was washed with 1 mL of MilliQ water after which octopamine was eluted with 2×0.25 mL ammonium hydroxide (4 M). The oxidation of octopamine to p-hydroxybenzaldehyde was carried out for 6 min with 100 µl sodium periodate (2%) and was stopped with 100 µl sodium metabisulfite (10%). Absorbance was measured at 330 nm on a Spectramax microplate reader (Molecular Devices, Sunnyvale, Calif.). All enzymatic reactions were performed in duplicate. Results are reported in the table below as activity in % of control at the inhibitor concentration tested.

Furthermore, the ability of a compound to inhibit DβH activity may be assessed in human plasma using the following assay. For the purposes of the present invention, a compound is considered to be a "DβH inhibitor" if it exhibits activity in "% of control" of ≤20% at 10 µm in this assay. Preferred compounds of the present invention (including most of the specific Examples above) exhibit activity in "% of control" of ≤50% at 1.0 µm in this cell assay. More preferred compounds of the present invention exhibit activity in "% of control" of ≤20% at 1.0 µm in this cell assay.

Especially preferred compounds of the present invention exhibit activity in "% of control" of ≤50% at 100 nm in this assay.

Dopamine beta hydroxylase activity in human plasma was measured by the method previously developed (Nagatsu, T. and Udenfriend, S. Photometric assay of dopamine-β-hydroxylase activity in human blood. *Clin. Chem.* 18(9) 980-983, 1972) with minor modifications. Catalase, N-ethylmaleimide, tyramine, disodium fumarate, pargyline, sodium acetate, ascorbic acid, copper sulfate and octopamine were obtained from Sigma Chemical Co., St. Louis, Mo. 63178. Human plasma samples were obtained from healthy donors (Instituto Português do Sangue Transplantação, Centro Sangue Transplantação, Porto, Portugal). From date of collection, plasma was stored at −80° C. until use. Test compounds were initially prepared in dimethyl sulfoxide at a concentration of 10 mM and diluted in dimethyl sulfoxide to the required concentrations. Test compounds were further diluted in ultrapure water to a concentration 20-fold to that of the final concentration to be tested. Final concentrations of test compounds were 10, 100 and 1000 nM. The various reagents used to make up the incubation buffer were premixed and consisted of the following components: sodium acetate buffer (1 M, pH 5.0, 18 ml), sodium fumarate (0.2 M, 4.5 ml), ascorbic acid (0.2 M, 4.5 ml, freshly prepared), pargyline (20 mM, freshly prepared, 4.5 ml), N-ethylmaleimide (0.2 M, 4.5 ml), catalase (10 000 U/ml, 9 ml), copper sulfate (20 µM, 4.5 ml) and 4.5 ultrapure water. The standard incubation mixture (total volume, 950 µl) contained: 50 µL of compound or vehicle (dimethyl sulfoxide 2%); 700 µL of incubation buffer; 125 µl of plasma (or saline for blank reaction or standard curve); 75 µl of saline. The reaction mixture was placed in water bath, shaking at 37° C. and pre-incubated for 10 minutes. Tyramine (0.5 M) was added and incubation proceeded for 45 minutes. The reaction contents were exposed to air. A sample of enzyme preparation (with 125 µl of plasma) that had been added perchloric acid 2 M at the end of the pre-incubation period was used as blank. A blank for each of the tested compounds was used. For octopamine standard curve, perchloric acid 2 M was replaced by increasing concentrations of octopamine prepared in perchloric acid 2 M (0.5, 1, 2.5, 5, 7.5, 10, 15, 20 µg/ml, final concentration). The incubation was stopped by adding 200 µl of 2 M molar perchloric acid, and the mixture was centrifuged at 9000 g for 5 min. The supernatant fluid (800 µL) was transferred to a column (SPE cartridge ISO-LUTE SCX-3, 100 mg) and centrifuged at 150 g for 2 min. The column was washed two more times with 0.5 ml of ultrapure water by centrifuging at 150 g for 2 min. The adsorbed octopamine was eluted twice with 0.3 ml of 4 M ammonium hydroxide by centrifuging at 150 g for 2 min. Octopamine in the eluate was then converted to p-hydroxybenzaldehyde by adding 200 µl of sodium periodate (2%) and incubating for 6 min. Excess periodate was than reduced by adding 200 µl of sodium metabisulfite (10%). Absorbance was measured at 330 mm in a 96-well plate by use of a SpectraMAX plus 384 (Molecular Devices) with software SOFTmax® PRO Software 5.3 spectrophotometer. Absorbance was linear with octopamine concentration from 0.5 to 20 µg/ml. Dopamine beta hydroxylase activity is determined as nmol of octopamine formed/ml of plasma/hour and effect of compounds is presented as % control.

Results are reported in the table below (inside brackets) as activity in % of control at the inhibitor concentration tested.

H. Biological Data

In Vitro Experiments:

| Example | DβH activity in % of Ctrl (0.1 μM) | DβH activity in % of Ctrl (1 μM) |
|---|---|---|
| 1 |  | 10.9 |
| 2 |  | 13.0 |
| 3 |  | 56.7 |
| 4 |  | 28.9 |
| 5 | 32.0 (57.3)* | 15.0 |
| 6 | 41.9 (74.1)* | 7.9 |
| 7 |  | 39.9 |
| 8 | 31.6 (38.3)* | 1 |
| 9 | 0 | 0 |
| 10 | 47.5 | 6.0 |
| 11 | 17.4 | 0 |
| 12 | 5.2 | 0 |
| 13 | (9.8)* |  |
| 14 | (4.7)* |  |
| 15 | (23.8)* |  |
| 16 | (12.1)* |  |
| 17 | (49.9)* |  |
| 18 | (10.0)* |  |
| 19 | (39.1)* |  |
| 20 | (27.7)* |  |
| 21 | (88.8)* |  |
| 22 | (0.5)* |  |
| 23 | (67.0)* |  |

*numbers in brackets represent activity in % of control in human plasma assay

The invention claimed is:

1. A compound of formula Ia, or a pharmaceutically acceptable salt or solvate thereof:

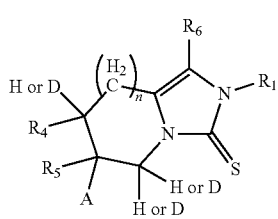

(Ia)

wherein:
- $R_1$ is hydrogen, $C_1$-$C_6$ alkyl, partially or fully deuterated $C_1$-$C_6$ alkyl, $C_3$-$C_6$ cycloalkyl, $C_2$-$C_6$ cyanoalkyl, $C_1$-$C_6$ mercaptoalkyl or amino;
- $R_4$ is hydrogen or $C_1$-$C_3$ alkyl;
- $R_5$ is hydrogen or $C_1$-$C_2$ alkyl;
- or $R_4$ and $R_5$ combine, together with the carbon atom to which they are attached, to form a cyclopropyl ring wherein the $CH_2$ moiety is optionally substituted with two deuterium atoms;
- $R_6$ is $C_1$-$C_6$ alkyl or partially or fully deuterated $C_1$-$C_6$ alkyl;
- A is $C_5$-$C_7$ cycloalkyl, furanyl, thiophenyl, methylthiophenyl or

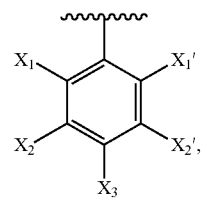

wherein:
- $X_1$ is hydrogen, halo or methyl;
- $X_1'$ is hydrogen or halo;
- $X_2$ is hydrogen, halo or methyl;
- $X_2'$ is hydrogen or halo;
- $X_3$ is hydrogen or fluoro;
- n is 0 or 1, and when n is 0 a single bond joins the carbon atoms to which the $CH_2$ moiety would be attached when n is 1.

2. The compound according to claim 1, wherein n is 0.

3. The compound according to claim 1, wherein $R_4$ and $R_5$ combine, together with the carbon atom to which they are attached, to form a cyclopropyl ring wherein the $CH_2$ moiety is optionally substituted with two deuterium atoms.

4. The compound according to claim 1, wherein more than 50% of substituents $R_5$ and A have the stereochemical configuration of formula Id

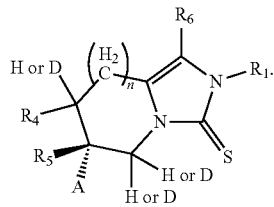

(Id)

5. The compound according to claim 1, wherein more than 50% of substituents $R_5$ and A have the stereochemical configuration of formula Ie

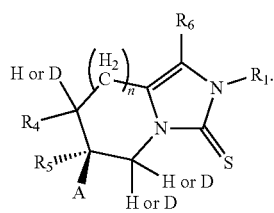

(Ie)

6. The compound according to claim 1, wherein A is

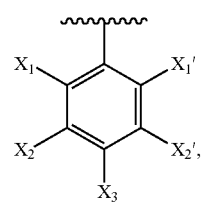

wherein $X_1$, $X_1'$, $X_2$, $X_2'$ and $X_3$ are as defined in claim 1.

7. The compound according to claim 1, wherein $R_1$ is hydrogen, methyl, d3-methyl, propyl, cyclopropyl, cyanomethyl, mercaptoethyl or amino.

8. The compound according to claim 1, wherein $R_4$ is hydrogen or methyl.

9. The compound according to claim 1, wherein $R_5$ is hydrogen or methyl.

10. The compound according to claim 1, wherein $R_6$ is methyl, n-butyl or $d_3$-methyl.

11. The compound according to claim 1, wherein A is

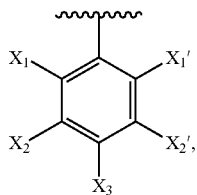

wherein:
$X_1$ is hydrogen, fluoro, chloro or methyl;
$X_1'$ is hydrogen, fluoro or chloro;
$X_2$ is hydrogen, fluoro, chloro, bromo or methyl;
$X_2'$ is hydrogen, fluoro, chloro or bromo;
$X_3$ is hydrogen or fluoro.

12. A method for treating or preventing conditions ameliorated by inhibition of dopamine-beta-hydroxylase comprising administering a therapeutically effective amount of a compound of formula Ia, as defined in claim 1, or a pharmaceutically acceptable salt or solvate thereof, to a patient in need thereof.

13. A pharmaceutical composition comprising (i) a therapeutically effective amount of a compound of formula Ia, as defined in claim 1, or a pharmaceutically acceptable salt or solvate thereof; and (ii) a pharmaceutically acceptable excipient.

14. The method according to claim 12, wherein the condition is a cardiovascular disorder.

15. The method according to claim 14, wherein the cardiovascular disorder is selected from the group consisting of hypertension, chronic heart failure and pulmonary arterial hypertension.

16. The method according to claim 12, wherein the condition is selected from the group consisting of cocaine addition, alcohol addition, adjunct opioid addiction, cognition decline in frontotemporal dementia, cognition decline in mild cognitive impairment, cognition decline in Alzheimer's disease, attention deficit-hyperactive disorder, post-traumatic stress disorder and unipolar depression.

17. The compound according to claim 1, wherein the compound is selected from the group consisting of:

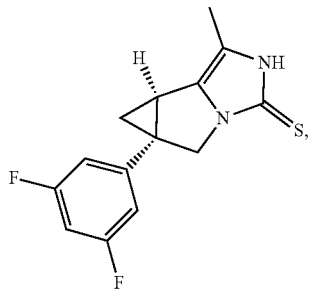

-continued

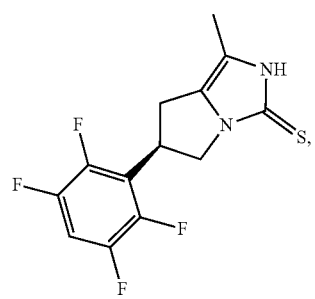

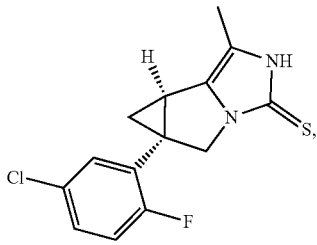

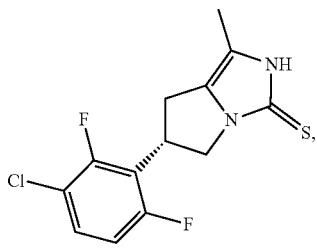

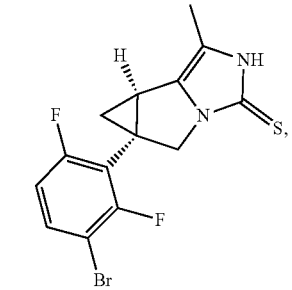

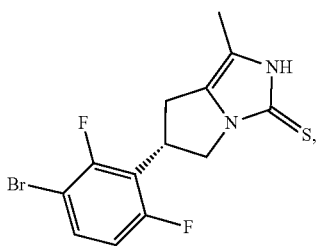

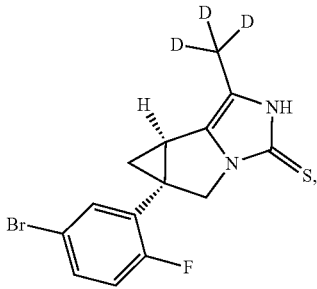

-continued

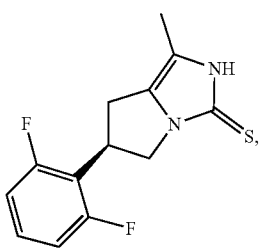

or a pharmaceutically acceptable salt or solvate thereof.

18. The compound according to claim 1, wherein the compound is

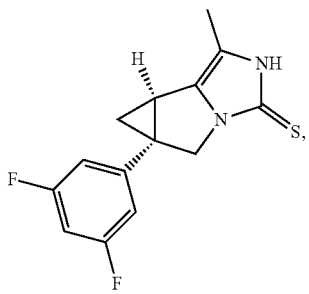 [SMILES: Cc1[nH]c(=S)n2c1[C@@H]1C[C@]1(c1cc(F)cc(F)c1)C2]

or a pharmaceutically acceptable salt or solvate thereof.

19. The compound according to claim 1, wherein the compound is

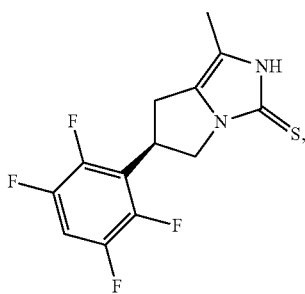 [SMILES: Cc1[nH]c(=S)n2c1C[C@H](c1c(F)c(F)cc(F)c1F)C2]

or a pharmaceutically acceptable salt or solvate thereof.

20. The compound according to claim 1, wherein the compound is

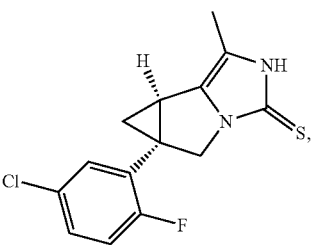 [SMILES: Cc1[nH]c(=S)n2c1[C@@H]1C[C@]1(c1cc(Cl)ccc1F)C2]

or a pharmaceutically acceptable salt or solvate thereof.

21. The compound according to claim 1, wherein the compound is

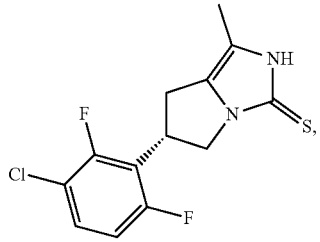 [SMILES: Cc1[nH]c(=S)n2c1C[C@@H](c1c(F)ccc(Cl)c1F)C2]

or a pharmaceutically acceptable salt or solvate thereof.

22. The compound according to claim 1, wherein the compound is

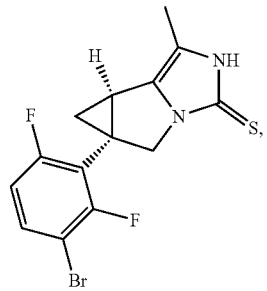 [SMILES: Cc1[nH]c(=S)n2c1[C@@H]1C[C@]1(c1c(F)ccc(Br)c1F)C2]

or a pharmaceutically acceptable salt or solvate thereof.

23. The compound according to claim 1, wherein the compound is

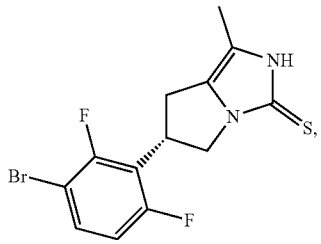

or a pharmaceutically acceptable salt or solvate thereof.

24. The compound according to claim 1, wherein the compound is

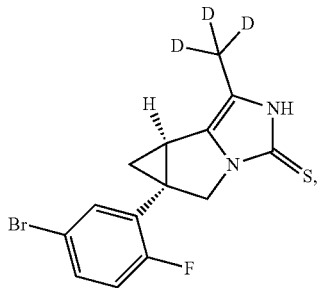 [SMILES: [2H]C([2H])([2H])c1[nH]c(=S)n2c1[C@@H]1C[C@]1(c1cc(Br)ccc1F)C2]

or a pharmaceutically acceptable salt or solvate thereof.

25. The compound according to claim 1, wherein the compound is
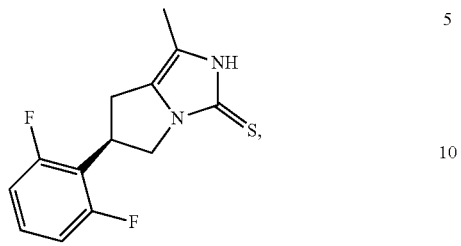
or a pharmaceutically acceptable salt or solvate thereof.
* * * * *

UNITED STATES PATENT AND TRADEMARK OFFICE
CERTIFICATE OF CORRECTION

| | |
|---|---|
| PATENT NO. | : 11,034,695 B2 |
| APPLICATION NO. | : 16/335529 |
| DATED | : June 15, 2021 |
| INVENTOR(S) | : Soares Da Silva et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 26 days.

Signed and Sealed this
Thirty-first Day of January, 2023

*Katherine Kelly Vidal*

Katherine Kelly Vidal
*Director of the United States Patent and Trademark Office*